(12) United States Patent
Sugiura et al.

(10) Patent No.: US 9,125,802 B2
(45) Date of Patent: Sep. 8, 2015

(54) DENTAL CURABLE COMPOSITION

(75) Inventors: Mariko Sugiura, Kurashiki (JP); Mitsuru Takei, Kurashiki (JP)

(73) Assignee: KURARAY NORITAKE DENTAL INC., Kurashiki-shi (JP)

( * ) Notice: Subject to any disclaimer, the term of this patent is extended or adjusted under 35 U.S.C. 154(b) by 114 days.

(21) Appl. No.: 13/996,360

(22) PCT Filed: Dec. 20, 2011

(86) PCT No.: PCT/JP2011/007125
§ 371 (c)(1),
(2), (4) Date: Jun. 20, 2013

(87) PCT Pub. No.: WO2012/086189
PCT Pub. Date: Jun. 28, 2012

(65) Prior Publication Data
US 2013/0274426 A1  Oct. 17, 2013

(30) Foreign Application Priority Data
Dec. 20, 2010  (JP) ................. 2010-283329
Sep. 26, 2011  (JP) ................. 2011-208960

(51) Int. Cl.
A61K 6/00    (2006.01)
A61K 6/083   (2006.01)

(52) U.S. Cl.
CPC .. *A61K 6/00* (2013.01); *A61K 6/083* (2013.01)

(58) Field of Classification Search
CPC ........... A61K 6/00; A61K 6/083; C08L 33/02
USPC ........................................ 523/109
See application file for complete search history.

(56) References Cited

U.S. PATENT DOCUMENTS

| | | | |
|---|---|---|---|
| 4,259,117 A | 3/1981 | Yamauchi et al. | |
| 4,539,382 A | 9/1985 | Omura et al. | |
| 4,544,359 A | 10/1985 | Waknine | |
| 4,547,531 A | 10/1985 | Waknine | |
| 4,548,689 A | 10/1985 | Sakashita et al. | |
| 4,719,297 A | 1/1988 | Henne et al. | |
| 6,953,535 B2 * | 10/2005 | Hecht et al. ............. | 252/183.13 |
| 2004/0097613 A1 | 5/2004 | Hecht et al. | |
| 2007/0040151 A1 | 2/2007 | Utterodt et al. | |
| 2012/0016094 A1 | 1/2012 | Takei et al. | |

FOREIGN PATENT DOCUMENTS

| | | |
|---|---|---|
| EP | 0 377 927 A1 | 7/1990 |
| JP | 52 113089 | 9/1977 |
| JP | 53 67740 | 6/1978 |
| JP | 53 69494 | 6/1978 |
| JP | 53 144939 | 12/1978 |
| JP | 58 128393 | 7/1983 |
| JP | 58 192891 | 11/1983 |
| JP | 61 83108 | 4/1986 |
| JP | 61 134307 | 6/1986 |
| JP | 61 148108 | 7/1986 |
| JP | 3 57916 | 9/1991 |
| JP | 2004 529947 | 9/2004 |
| JP | 2006 307151 | 11/2006 |
| JP | 2006307151 A * | 11/2006 |
| JP | 2007 56020 | 3/2007 |
| JP | 2009 263286 | 11/2009 |
| JP | 2009263286 A * | 11/2009 |
| JP | 2011 121869 | 6/2011 |
| WO | WO 2010/106903 A1 | 9/2010 |

OTHER PUBLICATIONS

English Translation of JP 2009-263286 obtained Jan. 15, 2015 at http://www19.ipdl.inpit.go.jp/PA1/cgi-bin/PA1DETAIL.*
English Translation of JP 2006-307151 obtained Jan. 15, 2015 at http://www19.ipdl.inpit.go.jp/PA1/cgi-bin/PA1DETAIL.*
International Search Report Issued Jan. 24, 2012 in PCT/JP11/007125 Filed Dec. 20, 2011.
Extended European Search Report issued May 4, 2015 in Patent Application No. 11851864.6.

* cited by examiner

*Primary Examiner* — Ling Choi
*Assistant Examiner* — Lanee Reuther
(74) *Attorney, Agent, or Firm* — Oblon, McClelland, Maier & Neustadt, L.L.P.

(57) ABSTRACT

The present invention provides a dental curable composition which has excellent curability and which cures into a cured product that is less susceptible to discoloration by hydrogen sulfide in an oral environment. The present invention is a dental curable composition containing: a polymerizable monomer (a) having an acidic group, as a polymerizable monomer component; and a copper compound (b) and a benzotriazole compound (c) represented by the following general formula (1) and/or a benzimidazole compound (c) represented by the following general formula (2), as polymerization initiator components (symbols used in the formulae are as described in the description).

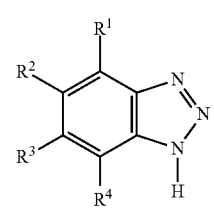

(1)

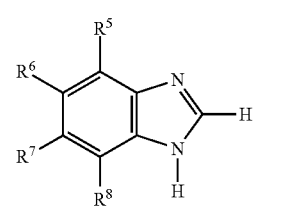

(2)

19 Claims, No Drawings

DENTAL CURABLE COMPOSITION

This application is a 371 of PCT/JP2011/007125 filed Dec. 20, 2011. Priority to Japanese patent application Nos. 2010-283329, filed Dec. 20, 2010; and 2011-208960, filed Sep. 26, 2011, are claimed.

TECHNICAL FIELD

The present invention relates to a dental curable composition containing a polymerizable monomer having an acidic group. More specifically, the present invention relates to a dental curable composition which has excellent curability and which cures into a cured product that is less susceptible to discoloration by hydrogen sulfide in an oral environment.

BACKGROUND ART

Curable compositions containing polymerizable monomers and radical polymerization initiators are widely used for dental curable compositions for use as dental cements, dental adhesives, composite resins, self-adhesive composite resins, sealants, dental autopolymerizing resins, etc.

Radical polymerization initiators are broadly classified into photopolymerization initiators and chemical polymerization initiators, and in recent years, dual cure products including both of them have been widely used in clinical practice. Among these radical polymerization initiators, chemical polymerization initiators are usually composed of a combination of an oxidizing agent and a reducing agent. When these oxidizing agent and reducing agent are mixed, a so-called redox reaction occurs to generate radicals, so that a polymerization reaction is initiated to promote the curing of a curable composition. A dental composition containing a redox polymerization initiator is usually separated into a composition containing an oxidizing agent and a composition containing a reducing agent for storage, and these compositions are mixed together just before use.

Compositions containing acidic components are usually used for dental curable compositions when they are used as dental cements, dental adhesives, self-adhesive composite resins, sealants, etc. that require adhesion to adherends. As redox polymerization initiators used in such compositions containing acidic components, radical polymerization initiators containing copper compounds have recently been proposed.

For example, Patent Literature 1 proposes a redox initiator containing a barbituric acid or thiobarbituric acid, a peroxodisulfate and/or peroxodiphosphate compound, a sulfinic acid compound, and a copper compound. Patent Literature 2 proposes a two-component initiator system including a hydroperoxide with a specific structure, a thiourea derivative, and a copper compound as an accelerator.

It is generally known that copper compounds are discolored and turned black by hydrogen sulfide produced by cariogenic bacteria in an oral environment. It is thus desirable to add traces of copper compounds for use in dental compositions.

According to the present inventors' studies, the redox initiator described in Patent Literature 1 has a drawback that even only use of a sulfinic acid compound and a copper compound can initiate a curing reaction, but in that case, the copper compound must be added at a high concentration to ensure the curability of the resulting composition and thus the composition is more susceptible to discoloration by hydrogen sulfide in an oral environment. The two-component initiator system described in Patent Literature 2 also has a drawback that at least a certain amount of a copper compound must be added to ensure the curability of the resulting composition and thus the composition is more susceptible to discoloration by hydrogen sulfide in an oral environment.

CITATION LIST

Patent Literature

Patent Literature 1: JP 2004-529947 T
Patent Literature 2: JP 2007-056020 A

SUMMARY OF INVENTION

Technical Problem

It is an object of the present invention to provide a dental curable composition which has excellent curability and which cures into a cured product that is less susceptible to discoloration by hydrogen sulfide in an oral environment.

Solution to Problem

In order to solve the above-mentioned problems, the present inventors have made intensive studies. As a result, the inventors have found that when a benzotriazole compound represented by the following general formula (1) and/or a benzimidazole compound represented by the following general formula (2) is added to a composition containing a copper compound and a polymerizable monomer having an acidic group, the catalytic activity of the copper compound is significantly improved and the reaction of the copper compound with hydrogen sulfide is suppressed, resulting in a composition which has excellent curability and which cures into a cured product that is less susceptible to discoloration by hydrogen sulfide in an oral environment, and have completed the present invention.

The present invention is a dental curable composition containing: a polymerizable monomer (a) having an acidic group, as a polymerizable monomer component; and a copper compound (b) and a benzotriazole compound (c) represented by the following general formula (1) and/or a benzimidazole compound (c) represented by the following general formula (2), as polymerization initiator components,

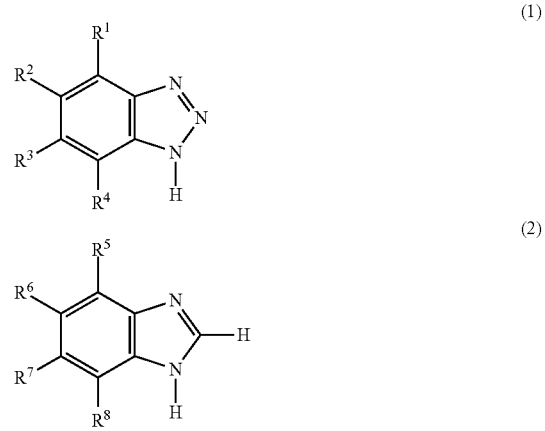

In these formulae, $R^1$ to $R^8$ are each independently a hydrogen atom, a hydroxyl group, an alkyl group, an aryl group, an alkoxy group, an alkenyl group, an aralkyl group, or a halogen atom.

Another aspect of the present invention is a dental curable composition containing: a polymerizable monomer (a) having an acidic group, as a polymerizable monomer component; and a copper salt of a benzotriazole compound (c) represented by the above general formula (1) and/or a benzimidazole compound (c) represented by the above general formula (2), as a polymerization initiator component.

Advantageous Effects of Invention

The dental curable composition of the present invention has excellent curability and a cured product thereof is less susceptible to discoloration by hydrogen sulfide in an oral environment.

DESCRIPTION OF EMBODIMENTS

The dental curable composition of the present invention contains a polymerizable monomer (a) having an acidic group, as a polymerizable monomer component, and contains a copper compound (b) and a benzotriazole compound (c) and/or a benzimidazole compound (c), as polymerization initiator components. First, these essential components are described.

As the polymerizable monomer (a) having an acidic group, there can be mentioned a polymerizable monomer having at least one acidic group such as a phosphate group, a pyrophosphate group, a thiophosphate group, a phosphonate group, a sulfonate group and a carboxylic acid group, and at least one polymerizable group such as an acryloyl group, a methacryloyl group, a vinyl group and a styrene group. The polymerizable monomer (a) having an acidic group has an affinity for an adherend and a tooth structure demineralization effect. It is preferable, from the viewpoint of polymerizability, that the polymerizable monomer (a) having an acidic group have an acryloyl group or a methacryloyl group as a polymerizable group. It is more preferable, from the viewpoint of safety for living bodies, that the polymerizable monomer (a) have a methacryloyl group. Specific examples of the polymerizable monomer (a) having an acidic group are as follows. In the following description, the term "(meth)acryl" refers to both "methacryl" and "acryl".

Examples of the polymerizable monomer having a phosphate group include 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyicosyl dihydrogen phosphate, bis[2-(meth)acryloyloxyethyl]hydrogen phosphate, bis[4-(meth)acryloyloxybutyl]hydrogen phosphate, bis[6-(meth)acryloyloxyhexyl]hydrogen phosphate, bis[8-(meth)acryloyloxyoctyl]hydrogen phosphate, bis[9-(meth)acryloyloxynonyl]hydrogen phosphate, bis[10-(meth)acryloyloxydecyl]hydrogen phosphate, 1,3-di(meth)acryloyloxypropyl dihydrogen phosphate, 2-(meth)acryloyloxyethylphenyl hydrogen phosphate, 2-(meth)acryloyloxyethyl 2-bromoethyl hydrogen phosphate, bis[2-(meth)acryloyloxy-(1-hydroxymethyl)ethyl]hydrogen phosphate, 2-methacryloyloxyethyl (4-methoxyphenyl)hydrogen phosphate, 2-methacryloyloxypropyl (4-methoxyphenyl)hydrogen phosphate, polymerizable monomers having a phosphate group described in JP 52 (1977)-113089 A, JP 53 (1978)-67740 A, JP 53 (1978)-69494 A, JP 53 (1978)-144939 A, JP 58 (1983)-128393 A and JP 58 (1983)-192891 A, and acid chlorides, alkali metal salts and ammonium salts of them.

Examples of the polymerizable monomer having a pyrophosphate group include bis[2-(meth)acryloyloxyethyl]pyrophosphate, bis[4-(meth)acryloyloxybutyl]pyrophosphate, bis[6-(meth)acryloyloxyhexyl]pyrophosphate, bis[8-(meth)acryloyloxyoctyl]pyrophosphate and bis[10-(meth)acryloyloxydecyl]pyrophosphate, and acid chlorides, alkali metal salts and ammonium salts of them.

Examples of the polymerizable monomer having a thiophosphate group include 2-(meth)acryloyloxyethyl dihydrogen thiophosphate, 3-(meth)acryloyloxypropyl dihydrogen thiophosphate, 4-(meth)acryloyloxybutyl dihydrogen thiophosphate, 5-(meth)acryloyloxypentyl dihydrogen thiophosphate, 6-(meth)acryloyloxyhexyl dihydrogen thiophosphate, 7-(meth)acryloyloxyheptyl dihydrogen thiophosphate, 8-(meth)acryloyloxyoctyl dihydrogen thiophosphate, 9-(meth)acryloyloxynonyl dihydrogen thiophosphate, 10-(meth)acryloyloxydecyl dihydrogen thiophosphate, 11-(meth)acryloyloxyundecyl dihydrogen thiophosphate, 12-(meth)acryloyloxydodecyl dihydrogen thiophosphate, 16-(meth)acryloyloxyhexadecyl dihydrogen thiophosphate and 20-(meth)acryloyloxyicosyl dihydrogen thiophosphate, and acid chlorides, alkali metal salts and ammonium salts of them.

Examples of the polymerizable monomer having a phosphonate group include 2-(meth)acryloyloxyethylphenyl phosphonate, 5-(meth)acryloyloxypentyl-3-phosphonopropyonate, 6-(meth)acryloyloxyhexyl-3-phosphonopropyonate, 10-(meth)acryloyloxydecyl-3-phosphonopropyonate, 6-(meth)acryloyloxyhexyl-3-phosphonoacetate and 10-(meth)acryloyloxydecyl-3-phosphonoacetate, and acid chlorides, alkali metal salts and ammonium salts of them.

Examples of the polymerizable monomer having a sulfonate group include 2-(meth)acrylamide-2-methylpropanesulfonic acid, styrenesulfonic acid, and 2-sulfoethyl(meth)acrylate.

Examples of the polymerizable monomer having a carboxylic acid group include a polymerizable monomer having one carboxyl group in a molecule and a polymerizable monomer having a plurality of carboxyl groups in a molecule.

Examples of the polymerizable monomer having one carboxyl group in a molecule include (meth)acrylic acid, N-(meth)acryloyl glycine, N-(meth)acryloyl aspartic acid, O-(meth)acryloyl tyrosine, N-(meth)acryloyl tyrosine, N-(meth)acryloylphenylalanine, N-(meth)acryloyl-p-aminobenzoic acid, N-(meth)acryloyl-o-aminobenzoic acid, p-vinylbenzoic acid, 2-(meth)acryloyloxybenzoic acid, 3-(meth)acryloyloxybenzoic acid, 4-(meth)acryloyloxybenzoic acid, N-(meth)acryloyl-5-aminosalicylic acid, N-(meth)acryloyl-4-aminosalicylic acid, 2-(meth)acryloyloxyethyl hydrogen succinate, 2-(meth)acryloyloxyethyl hydrogen phthalate and 2-(meth)acryloyloxyethyl hydrogen malate, and acid halides of them.

Examples of the polymerizable monomer having a plurality of carboxyl groups in a molecule include 6-(meth)acryloyloxyhexane-1,1-dicarboxylic acid, 9-(meth)acryloyloxynonane-1,1-dicarboxylic acid, 10-(meth)acryloyloxydecane-1,1-dicarboxylic acid, 11-(meth)acryloyloxyundecane-1,1-dicarboxylic acid, 12-(meth)acryloyloxydodecane-1,1-dicarboxylic acid, 13-(meth)acryloyloxytridecane-1,1-dicarboxylic acid, 4-(meth)acryloyloxyethyl trimellitate, 4-(meth)acryloyloxyethyl trimellitate anhydride, 4-(meth)acryloyloxybutyl trimellitate, 4-(meth)acryloyloxyhexyl trimellitate, 4-(meth)acryloyloxydecyl trimellitate and 2-(meth)acryloyloxyethyl-3'-(meth)acryloyloxy-2'-(3,4-dicarboxybenzoyloxy)propyl succinate, and acid anhydrides and acid halides of them.

The above-mentioned polymerizable monomers having an acidic group may be used alone or in combination. Among these polymerizable monomers having an acidic group, 10-(meth)acryloyloxydecyl dihydrogen phosphate, 1,3-di(meth)acryloyloxypropyl dihydrogen phosphate, 2-(meth)acryloyloxyethyl dihydrogen phosphate, 4-(meth)acryloyloxyethyl trimellitate anhydride, 4-(meth)acryloyloxyethyl trimellitate, 2-(meth)acrylamide-2-methylpropanesulfonic acid, and 11-(meth)acryloyloxyundecane-1,1-dicarboxylic acid are used preferably from the viewpoint of high bond strength to adherends.

The content of the polymerizable monomer (a) having an acidic group is preferably 1 to 50 parts by weight, more preferably 2 to 40 parts by weight, and further preferably 5 to 30 parts by weight, in 100 parts by weight of the total amount of polymerizable monomer components in the dental curable composition of the present invention. When the content of the polymerizable monomer having an acidic group is 1 part by weight or more, high adhesion to various adherends can easily be obtained. When the content of the polymerizable monomer having an acidic group is 50 parts by weight or less, polymerizability and adhesion are easily balanced. The total amount of polymerizable monomer components refers to the total amount of the polymerizable monomer (a) having an acidic group and a polymerizable monomer (f) having no acidic group, to be described below.

Preferably, the copper compound (b) is a compound which is soluble in the polymerizable monomer components. Specific examples of the copper compound include: copper carboxylates such as copper acetate, copper isobutyrate, copper gluconate, copper citrate, copper phthalate, copper tartrate, copper oleate, copper octylate, copper octanoate, copper naphthenate, copper methacrylate, and copper-4-cyclohexyl butyrate; copper β-diketones such as copper acetylacetonate, copper trifluoroacetylacetonate, copper hexafluoroacetylacetonate, copper 2,2,6,6-tetramethyl-3,5-heptanedionate, and copper benzoylacetone; copper β-ketoesters such as copper ethylacetoacetate; copper alkoxides such as copper methoxide, copper ethoxide, copper isopropoxide, copper 2-(2-butoxyethoxy)ethoxide, and copper 2-(2-methoxyethoxy)ethoxide; copper dithiocarbamates such as copper dimethyldithiocarbamate; salts of copper and inorganic acids such as copper nitrate; and copper chloride. These compounds can be used alone or in appropriate combination. Among these compounds, copper carboxylate, copper β-diketone and copper β-ketoester are preferable, and copper acetate and copper acetylacetonate are particularly preferable, from the viewpoints of solubility in and reactivity with the polymerizable monomers.

In the present invention, since the catalytic activity of the copper compound (b) is improved by a benzotriazole compound (c) and a benzimidazole compound (c) to be described below, the content of the copper compound (b) can be reduced more than before. Preferably, the content of the copper compound (b) is 0.00001 to 1 part by weight per 100 parts by weight of the total amount of the polymerizable monomer components in the dental curable composition, from the viewpoints of bond strength to adherends and working time. With respect to the lower limit of the content, the content is more preferably 0.0001 part by weight or more, further preferably 0.00025 part by weight or more, and particularly preferably 0.0005 part by weight or more. With respect to the upper limit of the content, the content is more preferably 0.1 part by weight or less, and further preferably 0.005 part by weight or less.

The benzotriazole compound (c) and the benzimidazole compound (c) are represented by the following general formulae (1) and (2), respectively.

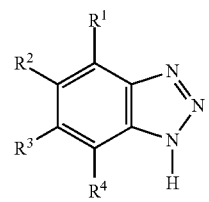

(1)

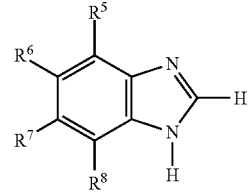

(2)

In the above general formulae (1) and (2), $R^1$ to $R^8$ are each independently a hydrogen atom, a hydroxyl group, an alkyl group, an aryl group, an alkoxy group, an alkenyl group, an aralkyl group, or a halogen atom.

The alkyl groups represented by $R^1$ to $R^8$ may be linear, branched or cyclic, and preferably they have 1 to 10 carbon atoms. Examples of the alkyl groups include a methyl group, an ethyl group, an n-propyl group, an isopropyl group, a cyclopropyl group, an n-butyl group, an isobutyl group, a sec-butyl group, a tert-butyl group, a cyclobutyl group, an n-pentyl group, an isopentyl group, a neopentyl group, a tert-pentyl group, a cyclopentyl group, an n-hexyl group, an isohexyl group, a cyclohexyl group, an n-heptyl group, a cycloheptanyl group, an n-octyl group, a 2-ethylhexyl group, a cyclooctyl group, an n-nonyl group, a cyclononyl group, and an n-decyl group. Among them, a methyl group and an ethyl group are particularly preferable.

Preferably, the aryl groups represented by $R^1$ to $R^8$ have 6 to 10 carbon atoms, and examples of them include a phenyl group, a naphthyl group, and an anthryl group.

The alkoxy groups represented by $R^1$ to $R^8$ may be linear, branched or cyclic, and preferably they have 1 to 8 carbon atoms. Examples of the alkoxy groups include a methoxy group, an ethoxy group, an n-propoxy group, an isopropoxy group, an n-butoxy group, a tert-butoxy group, an n-hexyloxy group, a cyclohexyloxy group, an n-octyloxy group, and a 2-ethylhexyloxy group.

The alkenyl groups represented by $R^1$ to $R^8$ may be linear, branched or cyclic, and preferably they have 1 to 6 carbon atoms. Examples of the alkenyl groups include a vinyl group, an allyl group, a methylvinyl group, a propenyl group, a butenyl group, a pentenyl group, a hexenyl group, a cycropropenyl group, a cyclobutenyl groupl, a cyclopentenyl group, and a cyclohexenyl group.

Examples of the aralkyl groups represented by $R^1$ to $R^8$ include an alkyl group (in particular, an alkyl group having 1 to 10 carbon atoms) substituted by an aryl group (in particular, an aryl group having 6 to 10 carbon atoms). A specific example is a benzyl group.

Examples of the halogen atoms represented by $R^1$ to $R^8$ include a chlorine atom, a bromine atom, and an iodine atom.

Preferably, $R^1$ to $R^8$ are hydrogen atoms or methyl groups.

These benzotriazole compounds (c) and the benzimidazole compounds (c) may be used alone or in combination. Specific examples of the benzotriazole compound (c) and the benzimidazole compound (c) include 1H-benzotriazole, 5-methyl-1H-benzotriazole, 5,6-dimethyl-1H-benzotriazole, benzimidazole, 5-methylbenzimidazole, and 5,6-dimethylbenzimidazole. Among these, 1H-benzotriazole and 5-methl-1H-benzotriazole are preferable in terms of the color tone and storage stability of the resulting composition.

The content of the compound (c) is preferably 0.01 to 10 parts by weight, more preferably 0.05 to 5 parts by weight, and most preferably 0.5 to 3 parts by weight, per 100 parts by weight of the total amount of the polymerizable monomer components in the dental curable composition, from the viewpoints of bond strength to adherends and working time.

The molar ratio between the content of the compound (c) and the content of the copper compound (b) is preferably 1:0.00001 to 1:0.01, and more preferably 1:0.0001 to 1:0.005. When the content ratio between the compound (c) and the copper compound (b) is in this range, better mechanical strength can be obtained while discoloration by hydrogen sulfide is suppressed.

The properties useful for dental applications can be improved by adding specific optional components to the dental curable composition of the present invention. Examples of these optional components include: a polymerizable monomer (f) having no acidic group as a polymerizable monomer component; an aromatic sulfinate (d), an organic peroxide (e), an inorganic peroxide (h), an amine-based reducing agent (i), and a sulfur-containing reducing inorganic compound (j), as polymerization initiator components; and a water-soluble organic solvent (g), water, and a filler (k), as other components. These components may be added alone or in combination to the dental curable composition.

Examples of the aromatic sulfinate (d) include lithium salts, sodium salts, potassium salts, rubidium salts, cesium salts, magnesium salts, calcium salts, strontium salts, iron salts, zinc salts, ammonium salts, tetramethyl ammonium salts and tetraethyl ammonium salts of benzene sulfinic acid, p-toluene sulfinic acid, o-toluene sulfinic acid, ethyl benzene sulfinic acid, decyl benzene sulfinic acid, dodecyl benzene sulfinic acid, 2,4,6-trimethyl benzene sulfinic acid, 2,4,6-triisopropyl benzene sulfinic acid, chlorobenzene sulfinic acid, and naphthalene sulfinic acid. Among these, lithium salts, sodium salts, potassium salts, magnesium salts and calcium salts of 2,4,6-trimethyl benzene sulfinic acid and 2,4,6-triisopropyl benzene sulfinic acid are preferable, and a lithium salt, a sodium salt, a potassium salt, a magnesium salt and a calcium salt of 2,4,6-triisopropyl benzene sulfinic acid are more preferable, in terms of the curability and storage stability of the composition.

Preferably, at least part of the aromatic sulfinate (d) is dispersed in powder form in the composition. Dispersion in powder form makes it possible to secure a longer working time for the dental curable composition of the present invention. Moreover, in the case where the dental curable composition is applied to tooth structure, the aromatic sulfinate (d) is dissolved in water on the surface of the tooth structure, and thus the curabilities through polymerization at the adhesion interface and inside the resin-dentin hybrid layer can be further increased. When the aromatic sulfinate (d) is dispersed in powder form, the aromatic sulfinate (d) preferably has a water solubility of 1 mg/100 mL or more at ordinary temperature (25° C.). In the case where the solubility is less than 1 mg/100 mL, when the dental curable composition of the present invention is applied to tooth structure, the aromatic sulfinate (d) is not sufficiently dissolved in the water on the tooth structure at the adhesion interface. As a result, the aromatic sulfinate (d) is less likely to exhibit the effect of dispersion in powder form. Since the aromatic sulfinate (d) tends to settle when its particle diameter is excessively large, the average particle diameter is preferably 500 µm or less, more preferably 100 µm or less, and further preferably 50 µm or less. However, the average particle diameter preferably is 0.01 µm or more because an excessively small average particle diameter excessively increases the specific surface area of the powder, which may cause deterioration in the handling of the curable composition. That is, in the case where the aromatic sulfinate (d) is dispersed in powder form, the powder preferably has an average particle diameter in the range of 0.01 to 500 µm, and more preferably in the range of 0.01 to 100 µm.

The average particle diameter of the aromatic sulfinate (d) refers to a mean volume particle diameter. The mean volume particle diameter can be calculated by, for example, image analysis on an electron micrograph of 100 or more particles, using an image analysis software (such as Mac-View produced by Mountech Co., Ltd.).

The shape of the aromatic sulfinate (d) when dispersed in powder form is not particularly limited, and may be any of various shapes such as spherical, needle-like, plate-like and crushed shapes. The aromatic sulfinate (d) in fine powder form may be produced by any of conventionally known methods such as a grinding method and a freeze-drying method.

Preferably, the content of the aromatic sulfinate (d) is 0.01 to 20 parts by weight per 100 parts by weight of the total amount of the polymerizable monomer components in the dental curable composition, from the viewpoints of bond strength to adherends and working time. When the content is less than 0.01 part by weight, the bond strength of the resulting composition to an adherend may decrease. The content is more preferably 0.05 part by weight or more, further preferably 0.1 part by weight or more, further more preferably 0.2 parts by weight or more, still more preferably 0.25 part by weight or more, and most preferably 0.3 part by weight of more. On the other hand, when the content exceeds 20 parts by weight, the handling of the resulting dental curable composition and the mechanical strength of the resulting cured product may decrease. The content is more preferably 15 parts by weight or less, further preferably 10 parts by weight or less, and most preferably 5 parts by weight or less.

In the case where the dental curable composition of the present invention contains the organic peroxide (e), the mechanical strength of the resulting cured product can be further increased.

As the organic peroxide (e), any known organic peroxide can be used without any particular limitation. Typical examples of the organic peroxide include hydroperoxide, peroxyester, ketone peroxide, peroxyketal, dialkyl peroxide, diacyl peroxide, and peroxydicarbonate. Among these, hydroperoxide and peroxyester are particularly preferable, and peroxyester is most preferable from the viewpoint of the storage stability of the resulting dental curable composition. These organic peroxides (e) may be used alone or in combination.

More specific examples of the hydroperoxide include cumene hydroperoxide, t-butyl hydroperoxide, t-hexyl hydroperoxide, p-menthane hydroperoxide, diisopropylbenzene hydroperoxide, and 1,1,3,3-tetramethylbutyl hydroperoxide.

As the peroxyester, any known peroxyester can be used without any limitation as long as it has an acyl group at one end of a peroxy group (—OO—) and a hydrocarbon group (or a similar group) at the other end thereof. Specific examples thereof include α,α-bis(neodecanoylperoxy)diisopropylbenzene, cumyl peroxyneodecanoate, 1,1,3,3-tetramethylbutyl peroxyneodecanoate, 1-cyclohexyl-1-methylethyl peroxyneodecanoate, t-hexyl peroxyneodecanoate, t-butyl peroxyneodecanoate, t-hexyl peroxypyvalate, t-butyl peroxypyvalate, 1,1,3,3-tetramethylbutyl peroxy-2-ethylhexanoate, 2,5-dimethyl-2,5-bis(2-ethylhexanoylperoxy)hexane, 1-cyclohexyl-1-methylethyl peroxy-2-ethylhexanoate, t-hexyl peroxy-2-ethylhexanoate, t-butyl peroxy-2-ethylhexanoate, t-butyl peroxyisobutyrate, t-hexyl peroxy isopropyl monocarbonate, t-butyl peroxy maleic acid, t-butyl peroxy-3,5,5-trimethylhexanoate, t-butyl peroxylaurate, 2,5-dimethyl-2,5-bis(m-toluoylperoxy)hexane, t-butyl peroxy isopropyl monocarbonate, t-butyl peroxy-2-ethylhexyl monocarbonate, t-hexyl peroxybenzoate, 2,5-dimethyl-2,5-bis(benzoylperoxy)hexane, t-butyl peroxyacetate, t-butyl peroxy-m-toluoylbenzoate, t-butyl peroxybenzoate, and bis(t-butylperoxy) isophthalate. These peroxyesters can be used alone or in combination. Among these, t-butyl peroxy maleic acid, t-butyl peroxy-3,5,5-trimethylhexanoate, t-butyl peroxybenzoate, t-butyl peroxy isopropyl monocarbonate, t-butyl peroxy-2-ethylhexyl monocarbonate, and t-butyl peroxyacetate are preferable, and t-butyl peroxybenzoate is more preferable, from the viewpoints of storage stability and reactivity.

Examples of the ketone peroxide include methyl ethyl ketone peroxide, cyclohexanone peroxide, methylcyclohexanone peroxide, methyl acetoacetate peroxide, and acetylacetone peroxide.

Examples of the peroxyketal include 1,1-bis(t-hexylperoxy)-3,3,5-trimethylcyclohexane, 1,1-bis(t-hexylperoxy)cyclohexane, 1,1-bis(t-butylperoxy)-3,3,5-trimethylcyclohexanone, 1,1-bis(t-butylperoxy)cyclohexane, 1,1-bis(t-butylperoxy)cyclododecane, 2,2-bis(t-butylperoxy)butane, n-butyl-4,4-bis(t-butylperoxy)valerate, and 2,2-bis(4,4-di-t-butylperoxycyclohexyl)propane.

Examples of the dialkyl peroxide include α,α-bis(t-butylperoxy)diisopropylbenzene, dicumyl peroxide, 2,5-dimethyl-2,5-bis(t-butylperoxy)hexane, t-butylcumyl peroxide, di-t-butyl peroxide, and 2,5-dimethyl-2,5-bis(t-butylperoxy)hexane-3.

Examples of the diacyl peroxide include isobutyryl peroxide, 2,4-dichlorobenzoyl peroxide, 3,5,5-trimethylhexanoyl peroxide, octanoyl peroxide, lauroyl peroxide, stearyl peroxide, succinic acid peroxide, m-toluoylbenzoyl peroxide, and benzoyl peroxide.

Examples of the peroxydicarbonate include di-n-propyl peroxydicarbonate, diisopropyl peroxydicarbonate, bis(4-t-butylcyclohexyl)peroxydicarbonate, di-2-ethoxyethyl peroxydicarbonate, di-2-ethylhexyl peroxydicarbonate, di-2-methoxybutyl peroxydicarbonate, and di(3-methyl-3-methoxybutyl)peroxydicarbonate.

The content of the organic peroxide (e) is preferably 0.001 to 10 parts by weight, more preferably 0.005 to 3 parts by weight, and further preferably 0.025 to 1 part by weight, per 100 parts by weight of the total amount of the polymerizable monomer components in the dental curable composition, from the viewpoints of bond strength to adherends and working time.

Examples of the inorganic peroxide (h) include peroxodisulfate and peroxodiphosphate. Among these, peroxodisulfate is preferable in terms of redox reactivity. Specific examples of the peroxodisulfate include sodium peroxodisulfate, potassium peroxodisulfate, aluminum peroxodisulfate, and ammonium peroxodisulfate.

The above-mentioned peroxodisulfates may be used alone or in combination. Among the above-mentioned peroxodisulfates, sodium peroxodisulfate, potassium peroxodisulfate, and ammonium peroxodisulfate are preferable.

Preferably, the inorganic peroxide (h) in powder form is added to the dental curable composition because the resulting dental curable composition has high storage stability. In this case, the average particle diameter of the powdery inorganic peroxide (h) is preferably in the range of 0.01 to 50 μm, and more preferably in the range of 0.1 to 20 μm. In the case where the powdery inorganic peroxide (h) has such an average particle diameter, the powdery inorganic peroxide (h) is efficiently dissolved in water on the surface of tooth structure at the adhesion interface. Therefore, it is possible to enhance selectively the curabilities through polymerization at the adhesion interface and inside the resin-dentin hybrid layer formed on the tooth structure, which are important for adhesion. The average particle diameter can be measured in the same manner as for the average particle diameter of the aromatic sulfinate (d) mentioned above.

The shape of the powdery inorganic peroxide (h) is not particularly limited, and may be any of various shapes such as spherical, needle-like, plate-like and crushed shapes. The powdery inorganic peroxide (h) can be produced by any of known methods such as a grinding method, a freeze-drying method, and a reprecipitation method. Among these methods of producing the powdery inorganic peroxide (h), the grinding method and the freeze-drying method are preferable, and the grinding method is more preferable, from the viewpoint of the average particle diameter of the resulting powder.

The content of the inorganic peroxide (h) is preferably 0.01 to 10 parts by weight per 100 parts by weight of the total amount of the polymerizable monomer components in the dental curable composition of the present invention. When the content is less than 0.01 part by weight, the bond strength may decrease. On the other hand, when the content exceeds 10 parts by weight, the bond strength and the mechanical strength of the resulting cured product may decrease.

The amine-based reducing agents (i) are broadly classified into aromatic amines and aliphatic amines, and in the present invention, either aromatic amines or aliphatic amines may be used. These amine-based reducing agents (i) may be used alone or in combination.

As the aromatic amine, known aromatic secondary amine, aromatic tertiary amine, etc. may be used. Examples of the aromatic secondary amine or aromatic tertiary amine include N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, and N,N-dimethyl-3,5-di-t-butylaniline. Among these, N,N-di(2-hydroxyethyl)-p-toluidine is preferable in terms of redox reactivity.

Examples of the aliphatic amine include: primary aliphatic amines such as n-butylamine, n-hexylamine, and n-octylamine; secondary aliphatic amines such as diisopropylamine, dibutylamine, and N-methylethanolamine; and tertiary aliphatic amines such as N-methyldiethanolamine, N-ethyldiethanolamine, N-n-butyldiethanolamine, N-lauryldiethanolamine, 2-(dimethylamino)ethyl (meth)acrylate, N-methyldiethanolamine di(meth)acrylate, N-ethyldiethanolamine di(meth)acrylate, triethanolamine tri(meth)acrylate, triethanolamine, trimethylamine, triethylamine, and tributylamine. Among these, the tertiary aliphatic amines are preferable in terms of redox reactivity, and N-methyldiethanolamine, triethanolamine, and 2-(dimethylamino)ethyl methacrylate are particularly preferable.

The content of the amine-based reducing agent (i) preferably is 0.01 to 10 parts by weight, more preferably 0.02 to 5 parts by weight, and most preferably 0.05 to 2 parts by weight per 100 parts by weight of the total amount of the polymerizable monomer components in the dental curable composition of the present invention. When the content is less than 0.01 part by weight, the bond strength of the resulting dental curable composition to tooth structure may decrease. On the other hand, when the content exceeds 10 parts by weight, the color tone stability of the resulting dental curable composition may decrease.

Examples of the sulfur-containing reducing inorganic compound (j) include sulfite, bisulfite, pyrosulfite, thiosulfate, thionate, and dithionite. Among these, sulfite and bisulfite are preferable. Specific examples include sodium sulfite, potassium sulfite, calcium sulfite, ammonium sulfite, sodium hydrogen sulfite, and potassium hydrogen sulfite. These sulfur-containing reducing inorganic compounds (j) may be used alone or in combination.

Preferably, at least part of the sulfur-containing reducing inorganic compound (j) is dispersed in powder form in the composition. Dispersion in powder form makes it possible to secure a longer working time for the dental curable composition of the present invention. Moreover, in the case where the dental curable composition is applied to tooth structure, the reducing inorganic compound (j) is dissolved in water on the surface of the tooth structure, and thus the curabilities through polymerization at the adhesion interface and inside the resin-dentin hybrid layer can be further increased. When the reducing inorganic compound (j) is dispersed in powder form, the reducing inorganic compound (j) preferably has a water solubility of 1 mg/100 mL or more at ordinary temperature (25° C.). In the case where the solubility is less than 1 mg/100 mL, when the dental curable composition of the present invention is applied to the tooth structure, the reducing inorganic compound (j) is not sufficiently dissolved in the water on the tooth structure at the adhesion interface. As a result, the reducing inorganic compound (j) is less likely to exhibit the effect of dispersion in powder form. Since the reducing inorganic compound (j) tends to settle when its particle diameter is excessively large, the average particle diameter is preferably 500 μm or less, more preferably 100 μm or less, and further preferably 50 μm or less. However, the average particle diameter preferably is 0.01 μm or more because an excessively small average particle diameter excessively increases the specific surface area of the powder, which may cause deterioration in the handling of the dental curable composition. That is, the reducing inorganic compound (j) in dispersed powder form preferably has an average particle diameter in the range of 0.01 to 500 μm, and more preferably in the range of 0.01 to 100 μm. The average particle diameter can be measured in the same manner as for the average particle diameter of the aromatic sulfinate (d) mentioned above.

The shape of the reducing inorganic compound (j) when dispersed in powder form is not particularly limited, and may be any of various shapes such as spherical, needle-like, plate-like and crushed shapes. Fine particles of the reducing inorganic compound (j) can be produced by any of known methods such as a grinding method and a freeze-drying method.

In the case where the dental curable composition of the present invention contains the components (b), (c), (d), (h), (i) and (j) as polymerization initiator components, the bond strength of the dental curable composition to tooth structure is particularly increased.

The content of the reducing inorganic compound (j) preferably is 0.01 to 15 parts by weight, more preferably 0.05 to 10 parts by weight, and most preferably 0.1 to 5 parts by weight per 100 parts by weight of the total amount of the polymerizable monomer components in the dental curable composition of the present invention. When the content is less than 0.01 part by weight, the bond strength of the resulting dental curable composition to the tooth structure may decrease. On the other hand, when the content exceeds 15 parts by weight, the mechanical strength of the resulting cured product of the dental curable composition may decrease.

The polymerizable monomer (f) having no acidic group is preferably a radical polymerizable monomer having a polymerizable group, and the polymerizable group is preferably a (meth)acryl group and/or a (meth)acrylamide group for the ease of radical polymerization. The dental curable composition of the present invention is used in oral cavity. Since the oral cavity is a wet environment, the polymerizable group may be detached by hydrolysis, etc. Therefore, in view of the stimulativeness to living bodies caused by the detached polymerizable group, the polymerizable group is preferably a methacryl group and/or a methacrylamide group. The polymerizable monomer (f) having no acidic group contributes to an improvement in the application workability and adhesion of the resulting composition and the mechanical strength of the cured composition.

As the polymerizable monomer (f) having no acidic group, the following water-soluble polymerizable monomers and hydrophobic polymerizable monomers can be mentioned.

The water-soluble polymerizable monomer refers to a monomer having a water solubility of 10% by weight or more at 25° C. Preferably, the solubility of the water-soluble polymerizable monomer is 30% by weight or more. More preferably, the water-soluble polymerizable monomer is soluble in water at an arbitrary ratio at 25° C. The water-soluble polymerizable monomer accelerates the penetration of the other components into the tooth structure. Also, the water-soluble polymerizable monomer itself penetrates into the tooth structure and adheres to an organic component (collagen) in the tooth structure. Examples of the water-soluble polymerizable monomer include 2-hydroxyethyl(meth)acrylate, 2-hydroxypropyl(meth)acrylate, 3-hydroxypropyl(meth)acrylate, 1,3-dihydroxypropyl(meth)acrylate, 2,3-dihydroxypropyl(meth)acrylate, 2-trimethylammoniumethyl(meth)acryl chloride, and polyethylene glycol di(meth)acrylate (having nine or more oxyethylene groups).

As the hydrophobic polymerizable monomer, there can be mentioned a crosslinkable polymerizable monomer having a water solubility of less than 10% by weight at 25° C. Examples thereof include an aromatic compound-type bifunctional polymerizable monomer, an aliphatic compound-type bifunctional polymerizable monomer, and tri-functional or higher polymerizable monomers. The hydrophobic polymerizable monomer enhances the handling of the resulting composition, the mechanical strength of the cured composition, etc.

Examples of the aromatic compound-type bifunctional polymerizable monomer include 2,2-bis((meth)acryloyloxyphenyl)propane, 2,2-bis[4-(3-(meth)acryloyloxy)-2-hydroxypropoxyphenyl]propane (commonly known as "Bis-GMA"), 2,2-bis(4-(meth)acryloyloxyethoxyphenyl)propane, 2,2-bis(4-(meth)acryloyloxypolyethoxyphenyl)propane, 2,2-bis(4-(meth)acryloyloxydiethoxyphenyl)

propane, 2,2-bis(4-(meth)acryloyloxytriethoxyphenyl) propane, 2,2-bis(4-(meth)acryloyloxytetraethoxyphenyl) propane, 2,2-bis(4-(meth)acryloyloxypentaethoxyphenyl) propane, 2,2-bis(4-(meth)acryloyloxydipropoxyphenyl) propane, 2-(4-(meth)acryloyloxydiethoxyphenyl)-2-(4-(meth)acryloyloxyethoxyphenyl)propane, 2-(4-(meth)acryloyloxydiethoxydiphenyl)-2-(4 (meth)acryloyloxytriethoxyphenyl)propane, 2-(4-(meth)acryloyloxydipropoxyphenyl)-2-(4-(meth)acryloyloxytriethoxyphenyl)propane, 2,2-bis(4-(meth)acryloyloxypropoxyphenyl)propane, 2,2-bis(4-(meth)acryloyloxyisopropoxyphenyl)propane, and 1,4-bis(2-(meth)acryloyloxyethyl)pyromeritate. Among these, 2,2-bis[4-(3-methacryloyloxy)-2-hydroxypropoxyphenyl]propane and 2,2-bis(4-methacryloyloxypolyethoxyphenyl)propane are preferable.

Examples of the aliphatic compound-type bifunctional polymerizable monomer include glycerol di(meth)acrylate, erythritol di(meth)acrylate, sorbitol di(meth)acrylate, mannitol di(meth)acrylate, pentaerythritol di(meth)acrylate, dipentaerythritol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, polyethylene glycol di(meth)acrylate, 1,3-butanediol di(meth)acrylate, 1,5-pentanediol di(meth)acrylate, 1,6-hexanediol di(meth)acrylate, 1,10-decanediol di(meth)acrylate, 2,2,4-trimethylhexamethylenebis(2-carbamoyloxyethyl) dimethacrylate (commonly known as "UDMA"), and 1,2-bis (3-methacryloyloxy-2-hydroxypropyloxy)ethane. Among these, glycerol di(meth)acrylate, triethylene glycol di(meth) acrylate, neopentyl glycol dimethacrylate, 2,2,4-trimethylhexamethylenebis(2-carbamoyloxyethyl)dimethacrylate, and 1,2-bis(3-methacryloyloxy-2-hydroxypropyloxy)ethane are preferable.

Examples of the trifunctional or higher polymerizable monomer include trimethylolpropane tri(meth)acrylate, trimethylolethane tri(meth)acrylate, trimethylolmethane tri (meth)acrylate, pentaerythritol tri(meth)acrylate, pentaerythritol tetra(meth)acrylate, dipentaerythritol tri(meth)acrylate, dipentaerythritol tetra(meth)acrylate, dipentaerythritol penta (meth)acrylate, N,N-(2,2,4-trimethylhexamethylene)bis[2-(aminocarboxy)propane-1,3-diol]tetramethacrylate, and 1,7-diacryloyloxy-2,2,6,6-tetraacryloyloxymethyl-4-oxyheptane.

The above-mentioned polymerizable monomers (f) having no acidic group (the water-soluble polymerizable monomers and the hydrophobic polymerizable monomers) may be added alone or in combination.

In the case where the dental curable composition of the present invention is used as a dental adhesive, it is preferable to use, as the polymerizable monomer (f) having no acidic group, the hydrophobic polymerizable monomer and the water-soluble polymerizable monomer mentioned above in combination. In that case, the content of the water-soluble polymerizable monomer is preferably in the range of 10 to 90 parts by weight, more preferably in the range of 20 to 70 parts by weight, and most preferably in the range of 30 to 60 parts by weight per 100 parts by weight of the total amount of the polymerizable monomer components in the dental curable composition. The content of the hydrophobic polymerizable monomer is preferably 9 to 60 parts by weight, more preferably 15 to 55 parts by weight, and further preferably 20 to 50 parts by weight per 100 parts by weight of the total amount of the polymerizable monomer components in the dental curable composition.

Also in the case where the dental curable composition of the present invention is used as a dental cement or a self-adhesive composite resin, it is preferable to use, as the polymerizable monomer (f) having no acidic group, the hydrophobic polymerizable monomer and the water-soluble polymerizable monomer mentioned above in combination. In that case, the content of the water-soluble polymerizable monomer is preferably in the range of 1 to 50 parts by weight, more preferably in the range of 2 to 40 parts by weight, and most preferably in the range of 5 to 30 parts by weight per 100 parts by weight of the total amount of the polymerizable monomer components in the dental curable composition. The content of the hydrophobic polymerizable monomer is preferably 10 to 95 parts by weight, more preferably 30 to 90 parts by weight, and further preferably 50 to 80 parts by weight in 100 parts by weight of the total amount of the polymerizable monomer components in the dental curable composition. Furthermore, it is preferable to use, as the above-mentioned polymerizable monomer (f) having no acidic group, the aromatic compound-type bifunctional polymerizable monomer with the water-soluble polymerizable monomer, and/or the aliphatic compound-type bifunctional polymerizable monomer in combination, from the viewpoints of the handling and transparency of the resulting dental curable composition and the mechanical strength of the cured composition, etc. When these monomers are used in combination, the ratio of their contents is not particularly limited. The content of the aromatic compound-type bifunctional polymerizable monomer is preferably 30 to 80 parts by weight, more preferably 40 to 75 parts by weight, and further preferably 50 to 70 parts by weight per 100 parts by weight of the total amount of the polymerizable monomer components in the dental curable composition. The content of the water-soluble polymerizable monomer is preferably 0 to 30 parts by weight, more preferably 2 to 25 parts by weight, and further preferably 5 to 20 parts by weight. The content of the aliphatic compound-type bifunctional polymerizable monomer is preferably 5 to 65 parts by weight, more preferably 7 to 50 parts by weight, and further preferably 10 to 35 parts by weight.

As the water-soluble organic solvent (g), an organic solvent having a water solubility of 5% by weight or more, and more preferably 30% by weight or more at 25° C. is used. An organic solvent that is soluble in water at an arbitrary ratio at 25° C. is used most preferably. In particular, the water-soluble organic solvent (g) having a boiling point of 100° C. or lower at normal pressure is preferable. Specific examples thereof include ethanol, methanol, 1-propanol, isopropyl alcohol, acetone, methyl ethyl ketone, 1,2-dimethoxyethane, 1,2-diethoxyethane, and tetrahydrofuran. These water-soluble organic solvents (g) may be added alone or in combination. The content of the water-soluble organic solvent (g) is preferably 200 parts by weight or less, more preferably 5 to 100 parts by weight, and further preferably 10 to 60 parts by weight per 100 parts by weight of the total amount of the polymerizable monomer components in the dental curable composition.

In the case where the dental curable composition of the present invention contains water, the water helps the polymerizable monomer (a) having an acidic group to demineralize the tooth structure. It is necessary to use water substantially free of impurities that adversely affect the adhesion, and distilled water or ion-exchanged water are preferable. An excessive content of water may decrease the adhesion, and preferably, the content of water is 40% by weight or less based on the total weight of the dental curable composition.

In the case where the dental curable composition of the present invention contains the filler (k), the workability and radiopacity of the composition, the mechanical strength and adhesion of the cured composition, etc. can be enhanced. Examples of the filler (k) include an inorganic filler, an organic filler, and a composite filler of an inorganic filler and an organic filler. These fillers (k) may be added alone or in combination.

Examples of the inorganic filler include: silica; minerals, such as kaoline, clay, isinglass and mica, containing silica as a base; and ceramics and glasses containing silica as a base and containing $Al_2O_3$, $B_2O_3$, $TiO_2$, $ZrO_2$, BaO, $La_2O_3$, SrO, ZnO, CaO, $P_2O_5$, $Li_2O$, $Na_2O$ or the like. As the glasses, lanthanum glass, barium glass, strontium glass, soda glass, lithium borosilicate glass, zinc glass, fluoroaluminosilicate glass, borosilicate glass, and bioglass are used suitably. Also, crystalline quartz, hydroxyapatite, alumina, titanium oxide, yttrium oxide, zirconia, calcium phosphate, barium sulphate, aluminium hydroxide, sodium fluoride, potassium fluoride, sodium monofluorophosphate, lithium fluoride, and ytterbium fluoride are used suitably. Fine particle silica having a primary particle diameter of 0.001 to 0.1 μm preferably are used from the viewpoints of adhesion and handling. Examples of commercially-available products of the fine particle silica include "Aerosil OX50", "Aerosil 50", "Aerosil 200", "Aerosil 380", "Aerosil R972" and "Aerosil 130" (trade names, all produced by Nippon Aerosil Co., Ltd.).

Examples of the organic filler include polymethyl methacrylate, polyethyl methacrylate, a polymer of multifunctional methacrylate, polyamide, polystyrene, polyvinyl chloride, chloroprene rubber, nitrile rubber, and styrene-butadiene rubber.

Examples of the composite filler of an inorganic filler and an organic filler include a composite filler obtained by dispersing an inorganic filler in an organic filler, and an inorganic/organic composite filler obtained by coating an inorganic filler with various polymers.

In order to enhance the curability, mechanical strength and application workability, the filler (k) may be used after the surface thereof is treated beforehand with a known surface-treating agent such as a silane coupling agent. Examples of the surface-treating agent include vinyltrimethoxysilane, vinyltriethoxysilane, vinyltrichlorosilane, vinyltri(β-methoxyethoxy)silane, γ-methacryloyloxypropyltrimethoxysilane, γ-glycidoxypropyltrimethoxysilane, γ-mercaptopropyltrimethoxysilane, and γ-aminopropyltriethoxysilane.

In the case where the dental curable composition of the present invention is used as a dental adhesive, fine particle silica having a primary particle diameter of 0.001 to 0.1 μm, among the above-mentioned fillers (k), is preferably used in terms of bond strength and application workability. The content of the filler (k) is preferably in the range of 0 to 20% by weight, and more preferably in the range of 1 to 10% by weight, based on the total weight of the dental curable composition.

On the other hand, in the case where the dental curable composition of the present invention is used as a dental cement or a self-adhesive dental composite resin, the content of the above-mentioned filler (k) is preferably in the range of 10 to 90% by weight based on the total weight of the dental curable composition in order to improve the handling, radiopacity, mechanical strength, etc. With respect to the lower limit of the content, the content is more preferably 30% by weight or more, further preferably 40% by weight or more, and most preferably 50% by weight or more. With respect to the upper limit of the content, the content is more preferably 85% by weight or less.

The dental curable composition of the present invention contains the above-mentioned chemical polymerization type polymerization initiator system. In order to prepare the dental curable composition of the present invention as a dual cure type composition in which polymerization is also initiated by irradiation with light, a conventionally known photopolymerization initiator may further be added to the dental curable composition of the present invention, in addition to the above-mentioned polymerization initiator system. Examples of the conventionally known photopolymerization initiator include α-diketones, ketals, thioxanthones, acylphosphine oxides, and α-aminoacetophenones.

Specific examples of the α-diketones include camphorquinone, benzyl, and 2,3-pentanedione.

Specific examples of the ketals include benzyl dimethylketal and benzyl diethylketal.

Specific examples of the thioxanthones include 2-chlorothioxanthone and 2,4-diethylthioxantone.

Specific examples of the acylphosphine oxides include 2,4,6-trimethylbenzoyldiphenylphosphine oxide, bis(2,4,6-trimethylbenzoyl)phenylphosphine oxide, dibenzoylphenylphosphine oxide, bis(2,6-dimethoxybenzoyl)phenylphosphine oxide, tris(2,4-dimethylbenzoyl)phosphine oxide, tris(2-methoxybenzoyl)phosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyl-bis(2,6-dimethylphenyl)phosphine oxide, 2,4,6-trimethylbenzoylethoxyphenylphosphine oxide, and a water-soluble acylphosphine oxide compound disclosed in JP 3 (1991)-57916 B.

Specific examples of the α-aminoacetophenones include 2-benzyl-2-dimethylamino-1-(4-morpholinophenyl)-butanone-1, 2-benzyl-2-diethylamino-1-(4-morpholinophenyl)-butanone-1, 2-benzyl-2-dimethylamino-1-(4-morpholinophenyl)-propanone-1, 2-benzyl-2-diethylamino-1-(4-morpholinophenyl)-propanone-1, 2-benzyl-2-dimethylamino-1-(4-morpholinophenyl)-pentanone-1, and 2-benzyl-2-diethylamino-1-(4-morpholinophenyl)-pentanone-1.

These photopolymerization initiators may be used alone or in combination. Preferably, the content of the photopolymerization initiator is 0.005 to 10 parts by weight per 100 parts by weight of the total amount of the polymerizable monomer components in the dental curable composition. With respect to the lower limit of the content, the content is more preferably 0.01 part by weight or more, and further preferably 0.1 part by weight or more. With respect to the upper limit of the content, the content is more preferably 5 parts by weight or less.

Furthermore, in order to enhance the photocurability, the photopolymerization initiator may be used in combination with a polymerization accelerator such as aldehydes, a thiol compound or an aminobenzoic acid ester compound.

Specific examples of the aldehydes include derivatives of terephthalaldehyde and benzaldehyde. Examples of the benzaldehyde derivative include dimethylaminobenzaldehyde, p-methyloxybenzaldehyde, p-ethyloxybenzaldehyde, and p-n-octyloxybenzaldehyde.

Specific examples of the thiol compound include 2-mercaptobenzoxazol, decanethiol, 3-mercaptopropyltrimethoxysilane, and thiobenzoic acid.

Specific examples of the aminobenzoic acid ester compound include 4-N,N-dimethylaminobenzoic acid ethyl ester, 4-N,N-dimethylaminobenzoic acid methyl ester, N,N-dimethylaminobenzoic acid n-butoxyethyl ester, 4-N,N-dimethylaminobenzoic acid 2-[(meth)acryloyloxy]ethyl ester, 4-N,N-dimethylaminobenzophenone, and butyl 4-dimethylaminobenzoate.

The above-mentioned amine-based reducing agents (i) serve also as polymerization accelerators for the photopolymerization initiators.

These polymerization accelerators may be used alone or in combination. The content of the polymerization accelerator is preferably in the range of 0.01 to 10 parts by weight, and more preferably in the range of 0.1 to 5 parts by weight per 100 parts by weight of the total amount of the polymerizable monomer components in the dental curable composition.

A fluoride ion-releasing material may further be added to the dental curable composition of the present invention to impart acid resistance to tooth structure. Examples of the fluoride ion-releasing material include a fluoride ion-releasing polymer such as a copolymer of methyl methacrylate and fluoride methacrylate, a fluoride ion-releasing material such as cetylamine hydrofluoride, and the fluoroaluminosilicate glass, sodium fluoride, potassium fluoride, sodium monofluorophosphate, lithium fluoride and ytterbium fluoride mentioned above as inorganic fillers.

Additives, such as a stabilizer (polymerization inhibitor), a colorant, a fluorescent agent and an ultraviolet absorber, may be added to the dental curable composition of the present invention. Moreover, an antibacterial material, such as cetylpyridinium chloride, benzalkonium chloride, (meth)acryloyloxydodecyl pyridinium bromide, (meth)acryloyloxyhexadecylpyridinium chloride, (meth)acryloyloxydecylammonium chloride and triclosan, may be added. A known dye or pigment may be added.

The dental curable composition of the present invention can be prepared not only as a single part type composition but also as a multi-part type composition divided into two or more parts. Preferably, the dental curable composition of the present invention is used as a two-liquid type composition composed of a first liquid component part and a second liquid component part, or a two-paste type composition composed of a first paste component (including a liquid component and a filler) part and a second paste component part, from the viewpoints of storage stability and workability.

In the case where the dental curable composition of the present invention is prepared as a multi-part type dental curable composition including a first part and a second part, it is preferable that the first part contain the polymerizable monomer (a) having an acidic group and the copper compound (b), and the second part contain the benzotriazole compound (c) and/or the benzimidazole compound (c) and the aromatic sulfinate (d). In this case, it is preferable that the first part further contain the organic peroxide (e). Preferably, the organic peroxide (e) is a peroxyester because excellent storage stability and high adhesion to tooth enamel and crown restoration materials can be obtained.

The weight ratio at which the first part and the second part is mixed is preferably 1:10 to 10:1 in terms of the curability of the resulting composition and the time (working time) available for the operation of bonding.

As described above, when the benzotriazole compound (c) and/or the benzimidazole compound (c) is added to the composition containing the polymerizable monomer (a) having an acidic group and the copper compound (b), the catalytic activity of the copper compound (b) is significantly improved and the reaction of the copper compound with hydrogen sulfide is suppressed. As a result, the resulting composition has excellent curability, and a cured product of the composition is less susceptible to discoloration by hydrogen sulfide in an oral environment and has excellent mechanical strength.

Since the catalytic activity of the copper compound (b) is improved, the content of the copper compound (b) can be reduced more than before. Thus, the resulting composition can have excellent curability while a cured product of the composition can be hardly susceptible to discoloration by hydrogen sulfide in an oral environment.

The reason why the co-presence of the copper compound (b) and the benzotriazole compound (c) and/or the banzimidazole compound (c) causes an increase in the catalytic activity of the copper compound (b) and a decrease in the reactivity thereof with hydrogen sulfide is that the benzotriazole compound (c) and/or the benzimidazole compound (c) is coordinated to or interacts with Cu of the copper compound (b).

Viewed from another aspect, the present invention is also a dental curable composition containing: the polymerizable monomer (a) having an acidic group, as a polymerizable monomer component; and a copper salt of the benzotriazole compound (c) represented by the above general formula (1) and/or the benzimidazole compound (c) represented by the above general formula (2), as a polymerization initiator component.

The polymerizable monomer (a) having an acidic group, the benzotriazole compound (c) and/or the benzimidazole compound (c) that forms a salt with copper, and other optional components contained in this dental curable composition are the same as those described above. Preferably, the dental curable composition contains at least one selected from the group consisting of the aromatic sulfinate (d), the organic peroxide (e) and the polymerizable monomer (f) having no acidic group, as the other optional components. Particularly preferably, the composition contains the aromatic sulfinate (d).

Preferably, the content of the copper salt of the benzotriazole compound (c) and/or the benzimidazole compound (c) is 0.00001 to 1 part by weight per 100 parts by weight of the total amount of the polymerizable monomer components in the dental curable composition. With respect to the lower limit of the content, the content is more preferably 0.0001 part by weight or more, further preferably 0.00025 part by weight or more, and particularly preferably 0.0005 part by weight or more. With respect to the upper limit of the content, the content is more preferably 0.1 part by weight or less, and further preferably 0.05 part by weight or less.

A preferred embodiment of the dental curable composition of the present invention contains: the polymerizable monomer (a) having an acidic group and the polymerizable monomer (f) having no acidic group, as polymerizable monomer components; and the inorganic peroxide (h), the copper compound (b), the amine-based reducing agent (i), the aromatic sulfinate (d), and the benzotriazole compound (c) represented by the above general formula (1) and/or the benzimidazole compound (c) represented by the above general formula (2), as polymerization initiator components. This preferred composition not only has excellent curability and the effect of suppressing the discoloration of the resulting cured product by hydrogen sulfide produced by cariogenic bacteria but also has particularly excellent adhesion to dentin and enamel and imparts excellent mechanical strength to the cured product. This preferred composition is particularly suitable for dental cements.

If a product (particularly a dental cement) using this preferred composition is provided as a single part type product, the amine-based reducing agent (i) reacts with the inorganic peroxide (h) and decomposes the inorganic peroxide (h) during storage in some cases. The aromatic sulfinate (d) reacts with the copper compound (b) and decomposes the copper compound (b) in some cases. In these cases, the amount of radicals to be generated decreases. Therefore, the product using this preferred composition preferably is a two part type product including a first part and a second part. When this preferred composition is such a multi-part composition, it has a good working time.

In the preferred composition, the molar ratio between the content of the copper compound (b) and the content of the aromatic sulfinate (d) is preferably 0.000003:1 to 0.01:1, and more preferably 0.00003:1 to 0.005:1. When the ratio between the content of the copper compound (b) and the content of the aromatic sulfinate (d) is in this range, excellent mechanical strength can be obtained while practically preferred working time is maintained.

In the preferred composition, the content of the copper compound (b) is preferably 0.000001 to 0.01% by weight of the total amount of the polymerization initiator components. In the present invention, the polymerization initiator components refer to the components (b) to (e) and (h) to (j) including optional components.

When the preferred composition is divided into the first part and the second part, the first part contains the inorganic peroxide (h) and the second part contains the amine-based reducing agent (i) so that the inorganic peroxide (h) and the amine-based reducing agent (i) are contained in different parts, for example. The polymerizable monomer (a) having an acidic group and the polymerizable monomer (f) having no acidic group each may be contained in one or both of the first part and the second part. Here, from the viewpoint of storage stability, it is preferable that the polymerizable monomer (a) having an acidic group and the aromatic sulfinate (d) be contained in different parts. It is also preferable that one of the first and second parts (in particular, the first part) contain the polymerizable monomer (a) and optionally the polymerizable monomer (b) and the other part contain the polymerizable monomer (b) because the first and second parts in paste form are easier to handle. The compound (c) may be contained in one or both of the first part and the second part, but it is preferable that the copper compound (b) and the aromatic sulfinate (d) be contained in different parts from the viewpoint of storage stability. A suitable embodiment is, for example, an embodiment in which the first part contains the polymerizable monomer (a) having an acidic group, the inorganic peroxide (h), and the copper compound (b), and the second part contains the polymerizable monomer (f) having no acidic group, the amine-based reducing agent (i), the aromatic sulfinate (d), and the compound (c). In this case, when the composition contains a sulfur-containing reducing inorganic compound (j), it is preferable that the sulfur-containing reducing inorganic compound (j) be contained in the second part. When the composition contains the organic peroxide (e), it is preferable that the organic peroxide (e) be contained in the first part.

The weight ratio at which the first part and the second part is mixed is preferably 1:10 to 5:1 in view of the curability of the resulting composition and the time (working time) available for the operation of bonding.

When the product is a dental cement, it is preferable to add the filler (k) to the first part and/or the second part from the viewpoint of the mechanical strength of the cured product.

The above-mentioned preferred composition, even if it contains no water, can exhibit high bond strength by utilizing only water contained in the tooth structure. When the above-mentioned preferred composition contains water, the storage stability of the composition may decrease. Therefore, it is preferable that the above-mentioned preferred composition be substantially free from water. The phrase "to be substantially free from water" means that no water is added positively except for the water originally contained in each component of the composition. The content of water is, for example, 1% by weight or less based on the total weight of the composition.

When the dental curable composition of the present invention is used, only the dental curable composition is applied to an adherend surface, as a dental cement, a dental adhesive, a dental self-adhesive composite resin, or the like. In addition to this, the dental curable composition can be applied to an adherend surface to which another composition such as a primer has been applied.

Specific examples of the use of the dental curable composition of the present invention is described using a two part type product as an example. The first part and the second part are mixed together into a single part (the dental curable composition of the present invention) just before use, and then the composition is applied to tooth structure. When the composition thus mixed penetrates into the tooth structure, and a curing reaction also proceeds inside a wet body near the interface between the tooth structure and the dental curable composition. When the curing reaction is completed, the dental curable composition of the present invention and the tooth structure are bonded together. A detailed description of the application of the composition to a tooth is given below. In the case of filling a tooth cavity for restoration, the tooth cavity is cleaned by a common method, and then the dental curable composition of the present invention mixed into a single part is filled into the tooth cavity. In the case of attaching a prosthesis such as a crown or an inlay to an abutment tooth or a tooth cavity by luting, the adherend surface of the abutment tooth or the tooth cavity and the adherend surface of the prosthesis are cleaned, and then the dental curable composition of the present invention mixed into a single part is applied to at least one of the adherend surface of the abutment tooth or the tooth cavity and the adherend surface of the prosthesis. Thus, the prosthesis is attached to the tooth by luting. Before the dental curable composition of the present invention is applied to the tooth surface, the tooth surface may be subjected to a conventionally known pretreatment such as etching with an acidic aqueous solution, modification with a primer, and simultaneous etching/modification with a primer having etching capability.

EXAMPLES

The present invention will be described in detail below with reference to examples and comparative examples, but the present invention is not limited to these examples. The following abbreviations are used below.

[Polymerizable Monomer (a) Having an Acidic Group]
MDP: 10-methacryloyloxydecyl dihydrogen phosphate
4-META: 4-methacryloyloxyethyl trimellitate anhydride
[Copper Compound (b)]
CAA: copper (II) acetylacetonate
CA: copper (II) acetate
[Benzotriazole Compound (c)/Benzimidazole Compound (c)]
BTA: 1H-benzotriazole
MBTA: 5-methyl-1H-benzotriazole
BIA: benzimidazole
[Aromatic Sulfinate (d)]
TPBSS: sodium 2,4,6-triisopropylbenzenesulfinate
[Organic Peroxide (e)]
<Peroxyester>
BPB: t-butyl peroxybenzoate
BEC: t-butyl peroxy-2-ethylhexyl monocarbonate <Hydroperoxide>
CHP: cumene hydroperoxide
[Inorganic Peroxide (h)]
KPS: potassium peroxodisulfate: Potassium peroxodisulfate was crushed in a jet mill to obtain a powder having an average particle diameter of 2.5 μm. In these examples, the average particle diameter was determined as a mean volume particle diameter after an image analysis was made on an electron micrograph of 100 or more particles using an image analysis software (Mac-View; produced by Mountech Co., Ltd.).
[Amine-Based Reducing Agent (i)]
DEPT: N,N-di(2-hydroxyethyl)-p-toluidine
[Sulfur-Containing Reducing Inorganic Compound (j)]
Sodium sulfite: Sodium sulfite was ground in a vibratory ball mill to obtain a powder having an average particle diameter of 6.1 μm.
[Polymerizable Monomer (f) Having No Acidic Group]
<Hydrophobic Polymerizable Monomer>
Bis-GMA: 2,2-bis[4-(3-methacryloyloxy)-2-hydroxypropoxyphenyl]propane
D2.6E: 2,2-bis(4-methacryloyloxypolyethoxyphenyl)propane
GDMA: glycerol dimethacrylate
NPG: neopentyl glycol dimethacrylate
<Water-Soluble Polymerizable Monomer>
HEMA: 2-hydroxyethylmethacrylate
[Photopolymerization Initiator]
CQ: dl-camphorquinone
TMDPO: 2,4,6-trimethylbenzoyldiphenylphosphine oxide
PDE: N,N-dimethylaminobenzoic acid ethyl ester (a polymerization accelerator for the photopolymerization initiator)
[Polymerization Inhibitor]
BHT: 2,6-di-t-butyl-4-methylphenol
[Filler (k)]
F1: Silane-treated quartz powder
F2: Silane-treated barium glass powder
R972: Silica ("Aerosil R972" trade name, Nippon Aerosil Co., Ltd.)
Alumina: "Aluminum Oxide C" trade name, Nippon Aerosil Co., Ltd.
Silane-treated quartz powder (F1) and silane-treated barium glass powder (F2) were obtained in accordance with the following production methods.
Silane-treated quartz powder (F1):
Quartz (produced by MARUWA QUARTZ Co., Ltd.) was ground in a ball mill to obtain a quartz powder having an average particle diameter of about 4.5 μm. 100 parts by weight of this quartz glass powder was subjected to a surface treatment with 3 parts by weight of 3-methacryloyloxypropyltrimethoxysilane by a common method. Thus, a silane-treated quartz powder was obtained.
Silane-treated barium glass powder (F2):
Barium glass (produced by Esstech Inc., product code "Raysorb E-3000") was ground in a ball mill to obtain a barium glass powder having an average particle diameter of about 2.4 μm. 100 parts by weight of this barium glass powder was subjected to a surface treatment with 3 parts by weight of 3-methacryloyloxypropyltrimethoxysilane by a common method. Thus, a silane-treated barium glass powder was obtained.

Examples 1 to 8

The first part and the second part having respectively the compositions (all numeral values are expressed as parts by weight) shown in Table 1 were prepared. The dental curable composition (the composition of the present invention) was divided into two parts so that the weight ratio between these two parts was 1:1. The first part was prepared as follows. The components other than the filler were mixed together and then the mixture was stirred to obtain a homogeneous solution. The solution was mixed with the filler and the resulting mixture was degassed. The second part was prepared as follows. The components other than sodium 2,4,6-triisopropylbenzenesulfinate (hereinafter referred to as TPBSS) and the filler were mixed together and then the mixture was stirred to obtain a homogeneous solution. The solution was mixed with TPBSS and the filler and the resulting mixture was degassed. Each of the two-part dental curable compositions thus obtained was examined by the following methods, for the cement working time (T1), the change in the color tone of the cured cement by hydrogen sulfide water (C1) and the flexural strength of the cured cement (S1). Table 1 shows the results.

Comparative Examples 1 and 2

The first part and the second part having respectively the compositions shown in Table 1 were prepared. The dental curable composition (the composition for comparison) was divided into two parts so that the weight ratio between these two parts was 1:1. The first part and the second part were each prepared as follows. The components other than the filler were mixed together and then the mixture was stirred to obtain a homogeneous solution. The solution was mixed with the filler and the resulting mixture was degassed. Each of the two-part dental curable compositions thus obtained was examined for the cement working time (T1), the change in the color tone of the cured cement by hydrogen sulfide water (C1) and the flexural strength of the cured cement (S1) in the same manner as in Examples 1 to 8. Table 1 shows the results.

[Cement Working Time (T1)]

The first part and the second part were mixed at a weight ratio of 1:1 in a thermostat at 25° C., and the mixture was stirred with a spatula until well mixed into a single part. Time (working time) from when the first and second parts were mixed until the resulting paste started to cure and raised its temperature was measured with a thermocouple (manufactured by Okazaki Manufacturing Company) connected to a recorder (manufactured by Yokogawa Electric Corporation). Working time suitable for practical use is 2 to 8 minutes.

[Change in Color Tone of Cured Cement by Hydrogen Sulfide Water (C1)]

The first part and the second part were mixed at a weight ratio of 1:1, and the mixture was filled into a disk-shaped mold with a thickness of 1 mm and a diameter of 1.5 cm and allowed to stand still at 37° C. for 1 hour. Thus, a cured product was obtained. The color tone of the cured product thus obtained was determined as follows. Each specimen was placed on a white standard plate, and the chromaticity based on the L*a*b* color system was measured using a spectrophotometer ("SE 6000" trade name, manufactured by Nippon Denshoku Industries Co., Ltd.) that met the requirements of JIS-Z8729 under the conditions of a D65 light source with a 2° observer angle. The obtained values were defined as $L^*_0$, $a^*_0$, $b^*_0$, which were defined as an initial color tone. Next, this cured product was immersed in an "aqueous hydrogen sulfide solution" described below and stored in a closed container at 60° C. for 24 hours. Then, the cured product was taken out of the solution, water on the cured product was wiped off, and the chromaticity based on the L*a*b* color system was measured in the same manner as for the initial color tone. The color tone after the immersion was defined as $L^*_1$, $a^*_1$, $b^*_1$.

Discoloration caused by the reaction with hydrogen sulfide tends to decrease when a sample is left to stand in the clean atmosphere. Therefore, the chromaticity after the storage was measured within 10 minutes after the sample was taken out of the solution to the atmosphere. The resulting values were respectively substituted into the following formula to obtain a value ΔE* as a measure of discoloration.

$$\Delta E^* = \{(L^*_1 - L^*_0)^2 + (a^*_1 - a^*_0)^2 + (b^*_1 - b^*_0)^2\}^{1/2}$$

The "aqueous hydrogen sulfide solution" was prepared in the following manner. 0.6955 g of sodium sulfide nonahydrate (special grade chemical) was dissolved in distilled water to prepare 2 ml of aqueous sodium sulfide solution. Distilled water was added to 6.33 ml of 35 wt. % concentrated hydrochloric acid to prepare 100 ml of dilute hydrochloric acid. 1 ml of the above-mentioned aqueous sodium sulfide solution was put into a 10-ml sample tube, and then 4 ml of the above-mentioned dilute hydrochloric acid was added thereto. Then, the mixture was shaken to generate hydrogen sulfide. The solution in the sample tube at the generation of hydrogen sulfide (aqueous hydrogen sulfide solution) had a pH of 7.0 to 7.7. A simple pH meter ("Twin pH B-212" trade name, manufactured by Horiba, Ltd.) was used for the pH measurement. Since the pH of the solution increases as hydrogen sulfide is generated, the pH measurement was performed within 1 minute after the aqueous sodium sulfide solution and dilute hydrochloric acid were mixed, and the discoloration test was started 10 minutes after the mixing.

[Flexural Strength of Cured Cement (S1)]

A polyester film was laid over each of two glass slides, and a stainless steel mold with a length of 2 mm, a width of 25 mm and a depth of 2 mm was placed on one of the slides. Next, the composition obtained by kneading the first part and the second part at a weight ratio of 1:1 was filled into the mold. The surfaces of the composition in the mold were pressed between the glass slides through the polyester films, and the composition was clamped between the two glass slides with 25-mm alligator clips. The sample clamped with the alligator clips was allowed to stand still for 1 hour in a thermostat at 37° C. and to cure through polymerization. The sample was taken out of the thermostat, and the polymerized cured composition was removed from the mold. The polymerized cured product was immersed in distilled water at 37° C. for 24 hours for storage, and the resulting product was used as a specimen and subjected to a flexural test. The specimen was subjected to a three-point flexural test with a span of 20 mm at a crosshead speed of 1 mm/min. using a universal testing machine to measure the flexural strength. The average value of the five specimens was determined to be the flexural strength of the composition sample.

Examples 9 to 12 and Comparative Examples 3 and 4

The first part and the second part having respectively the compositions (all numeral values are expressed as parts by weight) shown in Table 2 were prepared. A two-liquid type dental adhesive containing these two parts at a weight ratio of 1:1 was produced. The first part and the second part were each prepared as follows. The components other than R972 were mixed together and then the mixture was stirred to obtain a homogeneous solution. The solution was mixed with R972 and the mixture was stirred. Each of the two-liquid type dental adhesives was examined by the following methods, for the bond working time (T2) and the change in the color tone of the cured bond by hydrogen sulfide water (C2). Table 2 shows the results.

[Bond Working Time (T2)]

0.1 g of the first part and 0.1 g of the second part were put in a hemispherical resin container with a diameter of 1 cm and a depth of 5 mm in a thermostat at 25° C., and they were stirred with a spatula until well mixed into a single part. Immediately after the mixing, a thermocouple (manufactured by Okazaki Manufacturing Company) connected to a recorder (manufactured by Yokogawa Electric Corporation) was put into this liquid mixture to record the temperature change accompanied by the polymerization curing reaction using the recorder. Thus, the curing time (time from when the two parts were mixed until the exothermic peak started) was determined. Working time suitable for practical use is 2 to 8 minutes.

[Change in Color Tone of Cured Bond by Hydrogen Sulfide Water (C2)]

The first part and the second part were mixed at a weight ratio of 1:1, and the mixture was dropped on a glass slide. Next, the dental adhesive was dried with a dental air syringe until it lost flowability, and then another glass slide was placed thereon with a 0.1-mm-thick metal spacer disposed therebetween. The adhesive was exposed to light irradiation for 20 seconds for curing with a dental light irradiator "JETLITE 3000" through the glass slide. After the light irradiation, the two glass slides were removed, and thus a cured product with a thickness of 0.1 mm and a diameter of about 1 cm was obtained. The color tone of the cured product obtained was measured with a photometer (SE6000: Nippon Denshoku), and the measured values were defined as the initial value of color tone. Next, this cured product was immersed in an "aqueous hydrogen sulfide solution" described below and stored in a closed container at 60° C. for 24 hours. Then, the cured product was taken out of the solution, water on the cured product was wiped off, and the color tone of the cured product was measured in the same manner as for the initial value. The values obtained were defined as the color tone after the immersion in hydrogen sulfide water. The difference (ΔE*) between the color tone after the immersion in hydrogen sulfide water and the initial value was defined as discoloration. The "aqueous hydrogen sulfide solution" was prepared in the same manner as the method described in the above paragraph "change in color tone of cured cement by hydrogen sulfide water (C1)".

TABLE 1

| | | | Example 1 | Example 2 | Example 3 | Example 4 | Example 5 |
|---|---|---|---|---|---|---|---|
| First part | Polymerizable monomer (a) having an acidic group | MDP | 20 | 20 | 20 | 20 | 20 |
| | | 4-META | — | — | — | — | — |
| | Polymerizable monomer (f) having no acidic group | Bis-GMA | 45 | 45 | 45 | 45 | 45 |
| | | HEMA | 35 | 35 | 35 | 35 | 35 |
| | Copper compound (b) | CA | 0.002 | 0.002 | 0.002 | 0.002 | 0.002 |
| | | CAA | — | — | — | — | — |
| | Peroxyester (e) | BPB | — | — | — | 1 | — |
| | | BEC | — | — | — | — | 1 |

TABLE 1-continued

|  |  |  |  |  |  |  |  |
|---|---|---|---|---|---|---|---|
|  | Hydroperoxide (e) | CHP | — | — | — | — | — |
|  | Photopolymerization initiator | CQ | 0.03 | 0.03 | 0.03 | 0.03 | 0.03 |
|  |  | TMDPO | 0.05 | 0.05 | 0.05 | 0.05 | 0.05 |
|  | Polymerization inhibitor | BHT | 0.05 | 0.05 | 0.05 | 0.05 | 0.05 |
|  | Filler (k) | F1 | 288 | 288 | 288 | 288 | 288 |
|  |  | R972 | 12 | 12 | 12 | 12 | 12 |
| Second part | Polymerizable monomer (f) having no acidic group | D2. 6E | 75 | 75 | 75 | 75 | 75 |
|  |  | NPG | 25 | 25 | 25 | 25 | 25 |
|  | Aromatic sulfinate (d) | TPBSS | 4 | 4 | 4 | 4 | 4 |
|  | Benzotriazole/benzimidazole compound (c) | BTA | 3 | — | — | 3 | 3 |
|  |  | MBTA | — | 3 | — | — | — |
|  |  | BIA | — | — | 3 | — | — |
|  | Photopolymerization initiator | PDE | 0.05 | 0.05 | 0.05 | 0.05 | 0.05 |
|  | Polymerization inhibitor | BHT | 0.05 | 0.05 | 0.05 | 0.05 | 0.05 |
|  | Filler (k) | F2 | 288 | 288 | 288 | 288 | 288 |
|  |  | Alumina | 12 | 12 | 12 | 12 | 12 |
| Cement working time (T1) (Min.) |  |  | 3.5 | 3.5 | 3.2 | 2.8 | 2.8 |
| Change in color tone of cured cement by hydrogen sulfide water (C1) (ΔE*) |  |  | 4.0 | 4.1 | 4.3 | 4.4 | 4.5 |
| Flexural strength of cured cement (S1) (MPa) |  |  | 105 | 102 | 108 | 117 | 118 |

|  |  |  | Example 6 | Example 7 | Example 8 | Com. Example 1 | Com. Example 2 |
|---|---|---|---|---|---|---|---|
| First part | Polymerizable monomer (a) having an acidic group | MDP | 20 | — | 20 | 20 | 20 |
|  |  | 4-META | — | 5 | — | — | — |
|  | Polymerizable monomer (f) having no acidic group | Bis-GMA | 45 | 55 | 45 | 45 | 45 |
|  |  | HEMA | 35 | 40 | 35 | 35 | 35 |
|  | Copper compound (b) | CA | 0.002 | 0.004 | — | 0.002 | 0.1 |
|  |  | CAA | — | — | 0.003 | — | — |
|  | Peroxyester (e) | BPB | — | — | — | — | — |
|  |  | BEC | — | — | — | — | — |
|  | Hydroperoxide (e) | CHP | 1 | — | — | — | — |
|  | Photopolymerization initiator | CQ | 0.03 | 0.03 | 0.03 | 0.03 | 0.03 |
|  |  | TMDPO | 0.05 | 0.05 | 0.05 | 0.05 | 0.05 |
|  | Polymerization inhibitor | BHT | 0.05 | 0.05 | 0.05 | 0.05 | 0.05 |
|  | Filler (k) | F1 | 288 | 288 | 288 | 288 | 288 |
|  |  | R972 | 12 | 12 | 12 | 12 | 12 |
| Second part | Polymerizable monomer (f) having no acidic group | D2. 6E | 75 | 75 | 75 | 75 | 75 |
|  |  | NPG | 25 | 25 | 25 | 25 | 25 |
|  | Aromatic sulfinate (d) | TPBSS | 4 | 4 | 4 | 4 | 4 |
|  | Benzotriazole/benzimidazole compound (c) | BTA | 3 | 3 | 3 | — | — |
|  |  | MBTA | — | — | — | — | — |
|  |  | BIA | — | — | — | — | — |
|  | Photopolymerization initiator | PDE | 0.05 | 0.05 | 0.05 | 0.05 | 0.05 |
|  | Polymerization inhibitor | BHT | 0.05 | 0.05 | 0.05 | 0.05 | 0.05 |
|  | Filler (k) | F2 | 288 | 288 | 288 | 288 | 288 |
|  |  | Alumina | 12 | 12 | 12 | 12 | 12 |
| Cement working time (T1) (Min.) |  |  | 2.9 | 3.1 | 3.4 | >10 | 3.7 |
| Change in color tone of cured cement by hydrogen sulfide water (C1) (ΔE*) |  |  | 4.3 | 5.6 | 4.3 | 6.4 | 33.4 |
| Flexural strength of cured cement (S1) (MPa) |  |  | 115 | 100 | 103 | — | 88 |

TABLE 2

|  |  |  | Example 9 | Example 10 | Example 11 | Example 12 | Com. Example 3 | Com. Example 4 |
|---|---|---|---|---|---|---|---|---|
| First part | Polymerizable monomer (a) having an acidic group | MDP | 20 | 20 | 10 | 10 | 20 | 20 |
|  | Polymerizable monomer (f) having no acidic group | Bis-GMA | 45 | 45 | 35 | 35 | 45 | 45 |
|  |  | HEMA | 35 | 35 | 25 | 25 | 35 | 35 |
|  | Copper compound (b) | CAA | 0.002 | 0.002 | 0.004 | 0.004 | 0.004 | 0.1 |
|  | Peroxyester (e) | BPB | — | 1 | — | 1 | — | — |
|  | Photopolymerization initiator | CQ | 2 | 2 | 2 | 2 | 2 | 2 |
|  |  | TMDPO | 1 | 1 | 1 | 1 | 1 | 1 |
|  | Others | Water | — | — | 10 | 10 | — | — |
|  | Polymerization inhibitor | BHT | 0.05 | 0.05 | 0.05 | 0.05 | 0.05 | 0.05 |
|  | Filler (k) | R972 | 5 | 5 | 5 | 5 | 5 | 5 |
| Second part | Polymerizable monomer (f) having no acidic group | Bis-GMA | 50 | 50 | — | — | 50 | 50 |
|  |  | GDMA | 20 | 20 | — | — | 20 | 20 |
|  |  | HEMA | 30 | 30 | — | — | 30 | 30 |
|  | Aromatic sulfinate (d) | TPBSS | 4 | 4 | 4 | 4 | 4 | 4 |
|  | Benzotriazole compound (c) | BTA | 3 | 3 | 3 | 3 | — | — |

TABLE 2-continued

|  |  | Example 9 | Example 10 | Example 11 | Example 12 | Com. Example 3 | Com. Example 4 |
|---|---|---|---|---|---|---|---|
| Photopolymerization initiator | PDE | 1.5 | 1.5 | 1.5 | 1.5 | 1.5 | 1.5 |
| Water-soluble organic solvent (g) | Ethanol | — | — | 50 | 50 | — | — |
| Others | Water | — | — | 50 | 50 | — | — |
| Polymerization inhibitor | BHT | 0.05 | 0.05 | 0.05 | 0.05 | 0.05 | 0.05 |
| Filler (k) | R972 | 5 | 5 | — | — | 5 | 5 |
| Bond working time (T2) (Min.) |  | 5.5 | 2.8 | 5.1 | 3.2 | >10 | 3.5 |
| Change in color tone of cured bond by hydrogen sulfide water (C2) (ΔE*) |  | 3.0 | 2.4 | 4.0 | 4.6 | 5.5 | 28.6 |

As shown in Table 1, the dental curable compositions of the present invention produced in Examples 1 to 8 each exhibited high curability in spite of a very low content of the copper compound and were less discolored in hydrogen sulfide water. On the other hand, the dental curable composition produced in Comparative Example 1 had a working time of more than 10 minutes, which was longer than the time suitable for practical use (2 to 8 minutes), and low curability, although it was less discolored in hydrogen sulfide water. Comparative Example 2 was more discolored in hydrogen sulfide water due to a high content of the copper compound, although it exhibited excellent curability.

As shown in Table 2, the dental curable compositions of the present invention produced in Examples 9 to 12 each exhibited high curability in spite of a very low content of the copper compound and were less discolored in hydrogen sulfide water. On the other hand, the dental curable composition produced in Comparative Example 3 had a working time of more than 10 minutes, which was longer than the time suitable for practical use (2 to 8 minutes), and low curability, although it was less discolored in hydrogen sulfide water. Comparative Example 4 was more discolored in hydrogen sulfide water due to a high content of the copper compound, although it exhibited excellent curability.

Examples 13 to 21

The first part and the second part having respectively the compositions shown in Table 3 were prepared. The dental curable composition was divided into two parts so that the weight ratio between these two parts was 1:1. The first part was prepared as follows. The components other than the powdery components (the filler and KPS) were mixed together and then the mixture was stirred to obtain a homogeneous solution. The solution was mixed with the powdery components and the resulting mixture was degassed. In the first part, the powdery components were dispersed in powder form. The second part was prepared as follows. The components other than the powdery components (the filler, TPBSS and sodium sulfite) were mixed together and then the mixture was stirred to obtain a homogeneous solution. The solution was mixed with the powdery components and the resulting mixture was degassed. In the second part, the powdery components were dispersed in powder form. Each of the two-part dental curable compositions (curable cement compositions) thus obtained was examined by the following methods, for the working time, the adhesion to bovine enamel, the adhesion to bovine dentin, the flexural strength of the cured product, and the discoloration of the cured cement after the immersion in hydrogen sulfide water. Table 3 shows the results.

[Working Time]

The first part and the second part were mixed at a weight ratio of 1:1 in a thermostat at 23° C., and the mixture was stirred with a spatula until well mixed into a single part. Time (working time) from when the first and second parts were mixed until the resulting paste started to cure and raised its temperature was measured with a thermocouple (manufactured by Okazaki Manufacturing Company) connected to a recorder (manufactured by Yokogawa Electric Corporation). Working time suitable for practical use is 2 to 8 minutes.

[Adhesion to Bovine Enamel]

The labial surface of a bovine mandibular incisor was ground with silicon carbide paper under running water so as to expose a flat surface of enamel. The exposed flat surface was further ground with #1000 silicon carbide paper under running water. After the grinding, water on the surface was air-blown to be dried. An adhesive tape with a thickness of about 150 μm having a circular hole whose diameter was 3 mm was attached to the smooth surface that had been dried and thereby the adherend area was defined. The first part and the second part of the divided curable composition were mixed together at a weight ratio of 1:1 to prepare a cement composition. A mound of the cement composition was formed on one end face (circular cross section) of a stainless steel cylindrical rod (with a diameter of 7 mm and a length of 2.5 cm). The end face with the mound of the cement composition formed thereon was placed on the smooth surface (adherend surface) in the circular hole so that the center of the hole and the center of the stainless steel cylindrical rod substantially coincided with each other, and the stainless steel cylindrical rod was pressed perpendicularly against the smooth surface to be bonded thereto. A test sample was thus prepared. Five samples were prepared in total. An excess portion of the cement composition forced out around the stainless steel cylindrical rod at the time of pressing the rod was removed, and then each sample was allowed to stand still at room temperature for 30 minutes and immersed in distilled water. The sample that had been immersed in distilled water was allowed to stand still for 24 hours inside a thermostat whose temperature was maintained at 37° C. The sample was examined for the tensile bond strength after it had been allowed to stand still at 37° C. for 24 hours. The tensile bond strength was measured with a universal testing machine (manufactured by Shimadzu Corporation) with the crosshead speed being set at 2 mm/min. Each of the tensile bond strengths shown in the table is an average of the values measured on the five test samples.

[Adhesion to Bovine Dentin]

The labial surface of a bovine mandibular incisor was ground with silicon carbide paper under running water so as to expose a flat surface of dentin. The exposed flat surface was further ground with #1000 silicon carbide paper under running water. After the grinding, water on the surface was air-blown to be dried. An adhesive tape with a thickness of about 150 μm having a circular hole whose diameter was 3 mm was attached to the smooth surface that had been dried and thereby the adherend area was defined. The first part and the second part of the divided curable composition were mixed together at a weight ratio of 1:1 to prepare a cement composition. A mound of the cement composition was formed on one end face (circular cross section) of a stainless steel cylindrical rod (with a diameter of 7 mm and a length of 2.5 cm). The end face with the mound of the cement composition formed thereon was placed on the smooth surface (adherend surface) in the circular hole so that the center of the hole and the center of the stainless steel cylindrical rod substantially coincided with each other, and the stainless steel cylindrical rod was pressed perpendicularly against the smooth surface to be bonded thereto. A test sample was thus prepared. Five samples were prepared in total. An excess portion of the cement composition forced out around the stainless steel cylindrical rod at the time of pressing the rod was removed, and then each sample was allowed to stand still at room temperature for 30 minutes and immersed in distilled water. The sample that had been immersed in distilled water was allowed to stand still for 24 hours inside a thermostat whose temperature was maintained at 37° C. The sample was examined for the tensile bond strength after it had been allowed to stand still at 37° C. for 24 hours. The tensile bond strength was measured with a universal testing machine (manufactured by Shimadzu Corporation) with the crosshead speed being set at 2 mm/min. Each of the tensile bond strengths shown in the table is an average of the values measured on the five test samples.

[Flexural Strength of Cured Product]

The flexural strength of each cured product was evaluated in the same manner as for the flexural strength of the cured cement (S1) described above.

[Discoloration of Cured Cement after Immersion in Hydrogen Sulfide Water]

The discoloration of each cured cement after immersion in hydrogen sulfide water was evaluated in the same manner as for the change in the color tone of the cured cement by hydrogen sulfide water (C1) described above.

As shown in Table 3, the use of the curable compositions of the present invention used in Examples 13 to 21 made it possible to achieve curability and excellent adhesion to dentin and enamel, and to obtain cured products having excellent mechanical strength. Discolorations of the cured products by hydrogen sulfide produced by cariogenic bacteria were suppressed although the curable compositions contained copper compounds, and the working times of the compounds were also good.

INDUSTRIAL APPLICABILITY

The dental curable composition of the present invention can be used as a dental adhesive, a dental cement, a composite resin, a self-adhesive composite resin, a sealant, a dental autopolymerizing resin, etc.

The invention claimed is:
1. A dental curable composition, comprising:
(a) a polymerizable monomer comprising an acidic group, as a polymerizable monomer component;
(b) a copper compound; and
(c) at least one of a benzotriazole compound represented by formula (I) and a benzimidazole compound represented by formula (II), as polymerization initiator components,

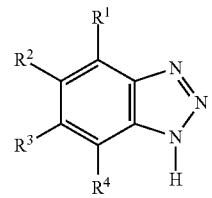

(I)

TABLE 3

| | | | Example 13 | Example 14 | Example 15 | Example 16 | Example 17 | Example 18 | Example 19 | Example 20 | Example 21 |
|---|---|---|---|---|---|---|---|---|---|---|---|
| First Part | (a) | MDP | 20 | 20 | 20 | 20 | 20 | 20 | 20 | 20 | 20 |
| | (f) | Bis-GMA | 40 | 40 | 40 | 40 | 40 | 40 | 40 | 40 | 40 |
| | | D2.6E | 20 | 20 | 20 | 20 | 20 | 20 | 20 | 20 | 20 |
| | | HEMA | 20 | 20 | 20 | 20 | 20 | 20 | 20 | 20 | 20 |
| | (h) | KPS | 1 | 1 | 1 | 2 | 2 | 2 | 2 | 1 | 1 |
| | (b) | CA | 0.001 | 0.001 | 0.001 | 0.001 | 0.001 | 0.001 | 0.001 | 0.005 | 0.0005 |
| | (e) | BPB | 0.5 | 0.5 | — | 0.5 | 0.5 | 0.5 | — | 0.5 | 0.5 |
| | Others | CQ | 0.03 | 0.03 | 0.03 | 0.03 | 0.03 | 0.03 | 0.03 | 0.03 | 0.03 |
| | | TMDPO | 0.05 | 0.05 | 0.05 | 0.05 | 0.05 | 0.05 | 0.05 | 0.05 | 0.05 |
| | | BHT | 0.1 | 0.1 | 0.1 | 0.1 | 0.1 | 0.1 | 0.1 | 0.1 | 0.1 |
| | (k) | F1 (Filler) | 215 | 215 | 215 | 215 | 215 | 215 | 215 | 215 | 215 |
| | | R972 | 15 | 15 | 15 | 15 | 15 | 15 | 15 | 15 | 15 |
| Second Part | (f) | D2.6E | 80 | 80 | 80 | 80 | 80 | 80 | 80 | 80 | 80 |
| | | NPG | 20 | 20 | 20 | 20 | 20 | 20 | 20 | 20 | 20 |
| | (i) | DEPT | 0.3 | 0.3 | 0.3 | 0.3 | 0.3 | 0.3 | 0.3 | 0.3 | 0.3 |
| | (d) | TPBSS | 2 | 2 | 2 | 2 | 4 | 4 | 4 | 4 | 4 |
| | (c) | BTA | 3 | 3 | 3 | 3 | 3 | 3 | 3 | 3 | 3 |
| | (j) | Sodium sulfite | 3 | — | 3 | 3 | 3 | — | — | 3 | 3 |
| | Others | PDE | 0.05 | 0.05 | 0.05 | 0.05 | 0.05 | 0.05 | 0.05 | 0.05 | 0.05 |
| | | BHT | 0.05 | 0.05 | 0.05 | 0.05 | 0.05 | 0.05 | 0.05 | 0.05 | 0.05 |
| | (k) | F2 (Filler) | 220 | 220 | 220 | 220 | 220 | 220 | 220 | 220 | 220 |
| | | Alumina | 10 | 10 | 10 | 10 | 10 | 10 | 10 | 10 | 10 |
| Working time (Min.) | 23° C. | | 3.5 | 3.5 | 4.5 | 2.5 | 2.0 | 2.0 | 3.0 | 2.5 | 4.5 |
| Adhesion to enamel (MPa) | 37° C. one day after | | 14.5 | 15.2 | 9.8 | 14.8 | 15.1 | 13.9 | 9.5 | 13.8 | 13.5 |
| Adhesion to dentin (MPa) | 37° C. one day after | | 11.5 | 7.9 | 10.3 | 12.0 | 12.5 | 10.6 | 10.4 | 11.3 | 11.1 |
| Flexural strength (MPa) | 37° C. one day after | | 102 | 115 | 91 | 107 | 110 | 112 | 105 | 112 | 98 |
| Discoloration of cured cement after immersion in hydrogen sulfide water ΔE* | | | 3.3 | 3.5 | 3.4 | 3.5 | 3.5 | 3.5 | 3.5 | 4.6 | 2.3 |

-continued

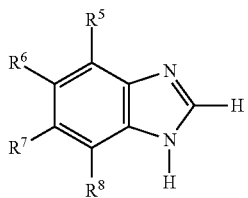
(II)

wherein R¹ to R⁸ are each independently a hydrogen atom, a hydroxyl group, an alkyl group, an aryl group, an alkoxy group, an alkenyl group, an aralkyl group, or a halogen atom.

2. The dental curable composition according to claim 1, further comprising: (d) an aromatic sulfinate.

3. The dental curable composition according to claim 2, wherein the dental curable composition is divided into:
a first part comprising the polymerizable monomer (a) comprising an acidic group and the copper compound (b); and
a second part comprising the aromatic sulfinate (d) and (c) at least one of the benzotriazole compound and the benzimidazole compound.

4. The dental curable composition according to claim 3, further comprising: (e) an organic peroxide in the first part.

5. The dental curable composition according to claim 4, wherein the organic peroxide (e) is a peroxyester.

6. The dental curable composition according to claim 1, further comprising: (f) a polymerizable monomer comprising no acidic group.

7. The dental curable composition according to claim 1, comprising 0.00001 to 1 part by weight of the copper compound (b) per 100 parts by weight of a total amount of polymerizable monomer components.

8. The dental curable composition according to claim 1, comprising:
the polymerizable monomer (a) comprising an acidic group and a polymerizable monomer (f) comprising no acidic group, as polymerizable monomer components; and
an inorganic peroxide (h), the copper compound (b), an amine-based reducing agent (i), an aromatic sulfinate (d), and (c) at least one of the benzotriazole compound and the benzimidazole compound, as polymerization initiator components.

9. The dental curable composition according to claim 8, comprising 0.00001 to 1 part by weight of the copper compound (b) per 100 parts by weight of a total amount of the polymerizable monomer components.

10. The dental curable composition according to claim 8, wherein the dental curable composition is divided into:
a first part comprising the polymerizable monomer (a) comprising an acidic group, the inorganic peroxide (h), and the copper compound (b); and
a second part comprising the polymerizable monomer (f) comprising no acidic group, the amine-based reducing agent (i), the aromatic sulfinate (d), and (c) at least one of the benzotriazole compound the benzimidazole compound.

11. The dental curable composition according to claim 10, further comprising: (j) a sulfur-comprising reducing inorganic compound as a polymerization initiator component in the second part.

12. The dental curable composition according to claim 10, further comprising: (e) an organic peroxide as a polymerization initiator component in the first part.

13. The dental curable composition according to claim 12, wherein the organic peroxide (e) is a peroxyester.

14. The dental curable composition according to claim 1, comprising said benzotriazole compound represented by formula (I).

15. The dental curable composition according to claim 1, comprising said benzimidazole compound represented by formula (II).

16. A dental curable composition, comprising:
(a) a polymerizable monomer comprising an acidic group, as a polymerizable monomer component; and
a copper salt of (c) at least one of a benzotriazole compound represented by formula (I) and a benzimidazole compound represented by formula (II), as a polymerization initiator component,

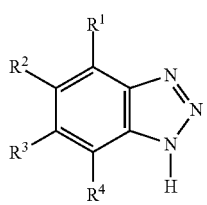
(I)

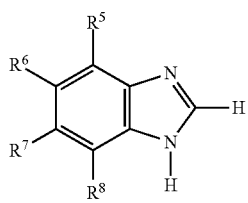
(II)

wherein R¹ to R⁸ are each independently a hydrogen atom, a hydroxyl group, an alkyl group, an aryl group, an alkoxy group, an alkenyl group, an aralkyl group, or a halogen atom.

17. The dental curable composition according to claim 16, further comprising: (d) an aromatic sulfinate.

18. The dental curable composition according to claim 16, comprising said copper salt of said benzotriazole compound represented by formula (I).

19. The dental curable composition according to claim 16, comprising said copper salt of said benzimidazole compound represented by formula (II).

* * * * *